(12) United States Patent
Togo et al.

(10) Patent No.: US 9,072,491 B2
(45) Date of Patent: Jul. 7, 2015

(54) SLEEP EVALUATION DEVICE AND SLEEP EVALUATION METHOD

(75) Inventors: Hidetaka Togo, Kyoto (JP); Yoko Kanemitsu, Ibaraki (JP); Yasuko Emori, Kyoto (JP); Masakazu Tsutsumi, Kyoto (JP); Feilang Tseng, Kyoto (JP); Toshiro Ito, Toki (JP)

(73) Assignee: OMRON HEALTHCARE CO., LTD., Muko-shi (JP)

( * ) Notice: Subject to any disclaimer, the term of this patent is extended or adjusted under 35 U.S.C. 154(b) by 0 days.

(21) Appl. No.: 13/982,441

(22) PCT Filed: Dec. 20, 2011

(86) PCT No.: PCT/JP2011/079520
§ 371 (c)(1),
(2), (4) Date: Jul. 29, 2013

(87) PCT Pub. No.: WO2012/124235
PCT Pub. Date: Sep. 20, 2012

(65) Prior Publication Data
US 2013/0324889 A1     Dec. 5, 2013

(30) Foreign Application Priority Data

Mar. 14, 2011   (JP) ................................ 2011-055470

(51) Int. Cl.
*A61B 5/00*   (2006.01)
*A61B 5/11*   (2006.01)

(52) U.S. Cl.
CPC ............ *A61B 5/4806* (2013.01); *A61B 5/4812* (2013.01); *A61B 5/11* (2013.01); *A61B 5/742* (2013.01)

(58) Field of Classification Search
USPC ............. 127/50; 340/575; 600/484, 529, 587, 600/595
See application file for complete search history.

(56) References Cited

U.S. PATENT DOCUMENTS

| | | | | | |
|---|---|---|---|---|---|
| 4,420,001 | A | * | 12/1983 | Hearne | 600/537 |
| 5,479,939 | A | * | 1/1996 | Ogino | 600/595 |
| 5,507,716 | A | * | 4/1996 | LaBerge et al. | 600/27 |
| 5,941,836 | A | * | 8/1999 | Friedman | 600/595 |
| 6,078,549 | A | * | 6/2000 | Wyatt et al. | 368/10 |
| 7,155,278 | B2 | * | 12/2006 | King et al. | 607/2 |
| 7,306,567 | B2 | * | 12/2007 | Loree, IV | 600/595 |

(Continued)

FOREIGN PATENT DOCUMENTS

| | | |
|---|---|---|
| CN | 101227858 A | 7/2008 |
| JP | A-2004-344265 | 12/2004 |

(Continued)

OTHER PUBLICATIONS

International Search Report issued in Application No. PCT/JP2011/079520; Dated Feb. 28, 2012 (With Translation).

(Continued)

*Primary Examiner* — Sean Dougherty
(74) *Attorney, Agent, or Firm* — Oliff PLC

(57) ABSTRACT

With an evaluation device, a sleep level of a person being measured is discriminated based on a signal input from a body motion sensor. With the evaluation device, when a go-to-bed button is operated at time T3, time T3 is stored as the go-to-bed time. When a good-night button is operated at time T4, discrimination of sleep level is started. Thereafter, when the good-night button again is operated at time T5, the discrimination of sleep level ends.

9 Claims, 20 Drawing Sheets

(56) References Cited

U.S. PATENT DOCUMENTS

| | | | |
|---|---|---|---|
| 7,415,100 B2* | 8/2008 | Cooper et al. | 379/88.01 |
| 7,460,899 B2* | 12/2008 | Almen | 600/509 |
| 7,522,035 B2* | 4/2009 | Albert | 340/521 |
| 7,572,225 B2* | 8/2009 | Stahmann et al. | 600/484 |
| 7,654,948 B2* | 2/2010 | Kaplan et al. | 600/26 |
| 7,898,426 B2* | 3/2011 | Rai et al. | 340/575 |
| 8,009,051 B2* | 8/2011 | Omi | 340/575 |
| 8,096,960 B2* | 1/2012 | Loree et al. | 600/595 |
| 8,323,218 B2* | 12/2012 | Davis et al. | 600/595 |
| 2001/0028309 A1* | 10/2001 | Torch | 340/575 |
| 2004/0225179 A1* | 11/2004 | Kaplan et al. | 600/26 |
| 2004/0230398 A1* | 11/2004 | Okada et al. | 702/182 |
| 2005/0076908 A1* | 4/2005 | Lee et al. | 128/204.23 |
| 2006/0169282 A1* | 8/2006 | Izumi et al. | 128/204.23 |
| 2006/0293608 A1* | 12/2006 | Rothman et al. | 600/545 |
| 2007/0273504 A1* | 11/2007 | Tran | 340/539.12 |
| 2008/0009685 A1* | 1/2008 | Kim et al. | 600/300 |
| 2008/0157956 A1* | 7/2008 | Radivojevic et al. | 340/531 |
| 2008/0191885 A1* | 8/2008 | Loree IV et al. | 340/575 |
| 2008/0275349 A1* | 11/2008 | Halperin et al. | 600/484 |
| 2008/0319354 A1* | 12/2008 | Bell et al. | 600/595 |
| 2009/0079561 A1* | 3/2009 | Nelson | 340/540 |
| 2009/0119841 A1* | 5/2009 | Takashima | 5/600 |
| 2009/0134819 A1 | 5/2009 | Noguchi et al. | |
| 2009/0149779 A1* | 6/2009 | Russo et al. | 600/595 |
| 2009/0240155 A1* | 9/2009 | Nakayama et al. | 600/500 |
| 2009/0273478 A1* | 11/2009 | Mei | 340/575 |
| 2009/0318779 A1* | 12/2009 | Tran | 600/301 |
| 2010/0102971 A1* | 4/2010 | Virtanen et al. | 340/575 |
| 2010/0328443 A1* | 12/2010 | Lynam et al. | 348/77 |
| 2011/0015495 A1* | 1/2011 | Dothie et al. | 600/300 |
| 2011/0018720 A1* | 1/2011 | Rai et al. | 340/575 |
| 2011/0112442 A1* | 5/2011 | Meger et al. | 600/595 |
| 2011/0163859 A1* | 7/2011 | Chraime et al. | 340/309.16 |
| 2011/0190594 A1* | 8/2011 | Heit et al. | 600/301 |
| 2011/0230790 A1* | 9/2011 | Kozlov | 600/595 |
| 2011/0267196 A1* | 11/2011 | Hu et al. | 340/575 |
| 2011/0275960 A1* | 11/2011 | Westerink et al. | 600/595 |
| 2012/0238800 A1* | 9/2012 | Naujokat et al. | 600/26 |
| 2013/0135108 A1* | 5/2013 | Alameh et al. | 340/575 |
| 2013/0235704 A1* | 9/2013 | Grinberg | 368/69 |

FOREIGN PATENT DOCUMENTS

| | | |
|---|---|---|
| JP | A-2007-054596 | 3/2007 |
| JP | 2007-199025 A | 8/2007 |
| JP | A-2007-195823 | 8/2007 |
| JP | A-2009-160001 | 7/2009 |

OTHER PUBLICATIONS

Sep. 3, 2014 Office Action issued in Chinese Patent Application No. 201180069083.4 (with translation).

Dec. 16, 2014 Office Action issued in Japanese Patent Application No. 2011-055470.

* cited by examiner

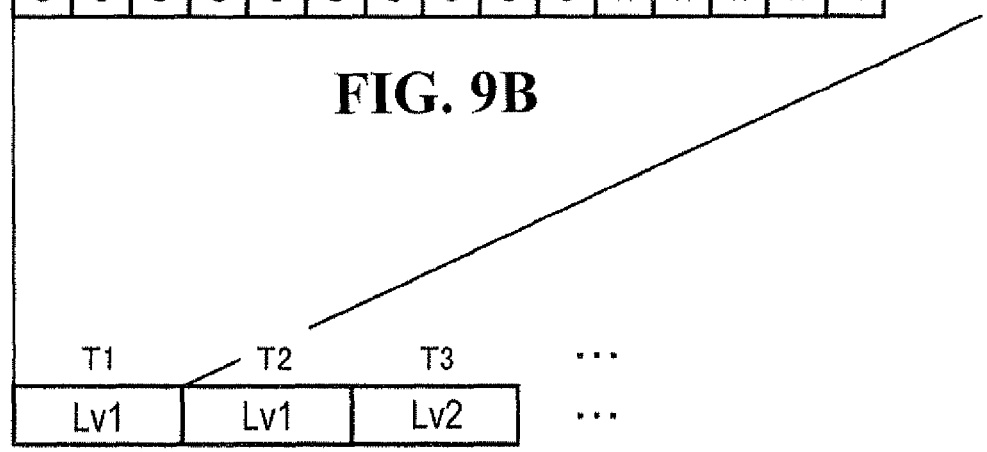

FIG. 10

| DATE | | SLEEP TIME | NIGHTTIME FROM PREVIOUS DAY | | | | | | | MORNING | | | | | | DAYTIME | | | | | WAKEUP TIME | SLEEPING DURATION | NOCTURNAL AWAKING | | MEAL TIME |
| --- | --- | --- | --- | --- | --- | --- | --- | --- | --- | --- | --- | --- | --- | --- | --- | --- | --- | --- | --- | --- | --- | --- | --- | --- | --- | --- |
| | | | 20 | 21 | 22 | 23 | 24 | 1 | 2 | 3 | 4 | 5 | 6 | 7 | 8 | 9 | 10 | 11 | 12 | 13 | | | FREQ | MIN | |
| 1 | MON | 2:36 | | | | | | | | | | | | | | | | | | | 10:26 | 7:01 | 7 | 29 | |
| 2 | TUES | 3:25 | | | | | | | | | | | | | | | | | | | 8:15 | 4:09 | 7 | 23 | |
| 3 | WED | 1:41 | | | | | | | | | | | | | | | | | | | 9:59 | 6:48:00 | 6 | 60 | |
| 4 | THURS | 2:07 | | | | | | | | | | | | | | | | | | | 8:04 | 5:35 | 3 | 13 | |
| 5 | FRI | 1:36 | | | | | | | | | | | | | | | | | | | 7:30 | 4:46 | 9 | 48 | |
| 6 | SAT | 1:41 | | | | | | | | | | | | | | | | | | | 12:10 | 8:43 | 12 | 60 | |
| 7 | SUN | 3:07 | | | | | | | | | | | | | | | | | | | 11:10 | 6:12 | 10 | 67 | |
| ### | TUES | 1:26 | | | | | | | | | | | | | | | | | | | 9:09 | 5:46 | 8 | 79 | |
| ### | WED | 2:29 | | | | | | | | | | | | | | | | | | | 8:36 | 4:23 | 6 | 78 | |

FIG. 12

| DATE | | PRE-SLEEP ACTIVITY | PRE-SLEEP DURATION | SLEEP LATENT DURATION |
|---|---|---|---|---|
| 1 | MON | YOGA | 1:00 | 0:45 |
| 2 | TUES | READING | 1:00 | 1:30 |
| 3 | WED | — | 0:00 | 0:10 |
| .. | .. | .. | .. | .. |

SLEEP EVALUATION DEVICE AND SLEEP EVALUATION METHOD

TECHNICAL FIELD

The invention relates to sleep evaluation devices and sleep evaluation methods, and particularly to sleep evaluation devices and sleep evaluation methods that evaluate the sleeping state of a person being measured in a non-invasive manner.

BACKGROUND ART

Heretofore, various techniques relating to devices for measuring sleep have been disclosed.

For example, Patent Literature 1 (JP 2009-160001A) discloses a device that measures temporal change in the body motion of a person being measured using sensors that are arranged under the bedding and that judges the state and quality of sleep of the person being measured based on the measurement results.

CITATION LIST

Patent Literature

Patent Literature 1: JP 2009-160001A

SUMMARY OF INVENTION

Technical Problem

However, according to the device, all measurement results given after the person being measured moves onto bedding are used as data for determining the state and quality of sleep. Therefore, for example, in the case where the person being measured is reading, doing light exercises such as stretching, and the like on the bed before going to sleep, a situation may occur in which even though the person being measured is awake on his/her own will, the device makes a mistaken evaluation of the sleeping state of the person being measured, for example, gives a determination result indicating that the person being measured has difficulty going to sleep, or the like.

It is an object of the present invention to improve the accuracy in the evaluation of the sleeping state of a person being measured in a sleep evaluation device.

Solution to Problem

A sleep evaluation device according to the present invention includes body motion detection means for detecting body motion of a person being measured on a bed, discrimination means for discriminating a sleeping state of the person being measured, based on a detection result of the body motion detection means, and input means that inputs information on the person being measured before going to sleep, and a sleeping state is discriminated based on the pre-sleep information and the detection result of the body motion detection means.

Preferably, the body motion detection means constantly detects the body motion of the person being measured on the bed, the pre-sleep information includes information specifying a timing at which the person being measured intends to end a state before sleeping, and the discrimination means starts the discrimination from said specified timing.

Preferably, the sleep evaluation device further includes body motion information storage means that stores information on the body motion detected by the body motion detection means, and a sleeping state is discriminated based on the body motion information stored in the body motion information storage means, the input means further receives information specifying a delete target period for which stored data of the body motion information is to be deleted from the body motion information storage means, and the body motion information storage means deletes stored data of the information specifying the body motion corresponding to the delete target period.

Preferably, the sleep evaluation device further includes period information storage means for storing information specifying a period during which the discrimination is performed by the discrimination means, and the discrimination means executes the discrimination in the period specified by the information stored in the period information storage means.

Preferably, the sleep evaluation device further includes body motion information storage means for storing information on the body motion detected by the body motion detection means, and the input means further receives information that instructs the body motion detection means to suspend detection, the body motion detection means suspends, in response to the information that instructs the suspension of the detection being input to the input means, the detection of body motion, and the body motion information storage means deletes stored data of the body motion information stored before the information is input, in response to the information that instructs the suspension of the detection being input to the input means.

Preferably, the pre-sleep information includes information specifying a first timing at which the person being measured is positioned on the bed, and information specifying a second timing at which the person being measured intends to end a state before sleeping, and the sleep evaluation device further includes arithmetic operation means that computes a first duration which is a duration from the first timing to the second timing.

Preferably, the sleep evaluation device specifies the first timing based on the detection result of the body motion detection means.

Preferably, the discrimination means further discriminates a sleep level of the sleeping state, the arithmetic operation means further computes a second duration which is a duration from the second timing to when the sleep level reaches a specific level, and the sleep evaluation device further includes display control means that displays the first duration and the second duration on a display device.

Preferably, the input means further receives information for specifying a type of activity done by the person being measured in a period from the first timing to the second timing, and the display control means displays on the display device said type of activity along with the first duration and the second duration.

The sleep evaluation method according to the present invention is a sleep evaluation method that is to be executed in a sleep evaluation device including body motion detection means for detecting body motion of a person being measured on a bed, and the sleep evaluation method includes a step of the body motion detection means detecting body motion of a person being measured on a bed, a step of receiving information on the person being measured before going to sleep, and a step of discriminating a sleeping state of the person being measured based on the pre-sleep information and the result of body motion detected by the body motion detection means.

Advantageous Effects of Invention

According to the present invention, discrimination means discriminates the sleeping state of a person being measured based on information on the person being measured before he/she goes to sleep that is input to input means.

Accordingly, the discrimination means is capable of avoiding, as much as possible, a situation in which periods other than the period that the person being measured desires to evaluate are evaluated, and thus the accuracy in evaluations of sleeping states performed by the sleep evaluation device can be improved.

BRIEF DESCRIPTION OF DRAWINGS

FIG. 9A is a diagram showing a specific example of discrimination results of a discrimination unit shown in FIG. 6, and FIG. 9B is a diagram showing a specific example of correction of discrimination results shown in FIG. 9A. FIG. 9C is a diagram showing a specific example of sleep level discrimination results for each fixed period.

FIG. 10 is a diagram showing a first specific example of the display of sleep levels.

FIG. 12 is a diagram showing a specific example of the display of types of pre-sleep activity, pre-sleep duration, and sleep latent duration.

DESCRIPTION OF EMBODIMENTS

Embodiments of the present invention will be described hereinafter, with reference to the drawings. In the following description, the same reference signs are given to the same components and constituent elements. The names and functions thereof are also the same.

External Appearance

Figure 1:
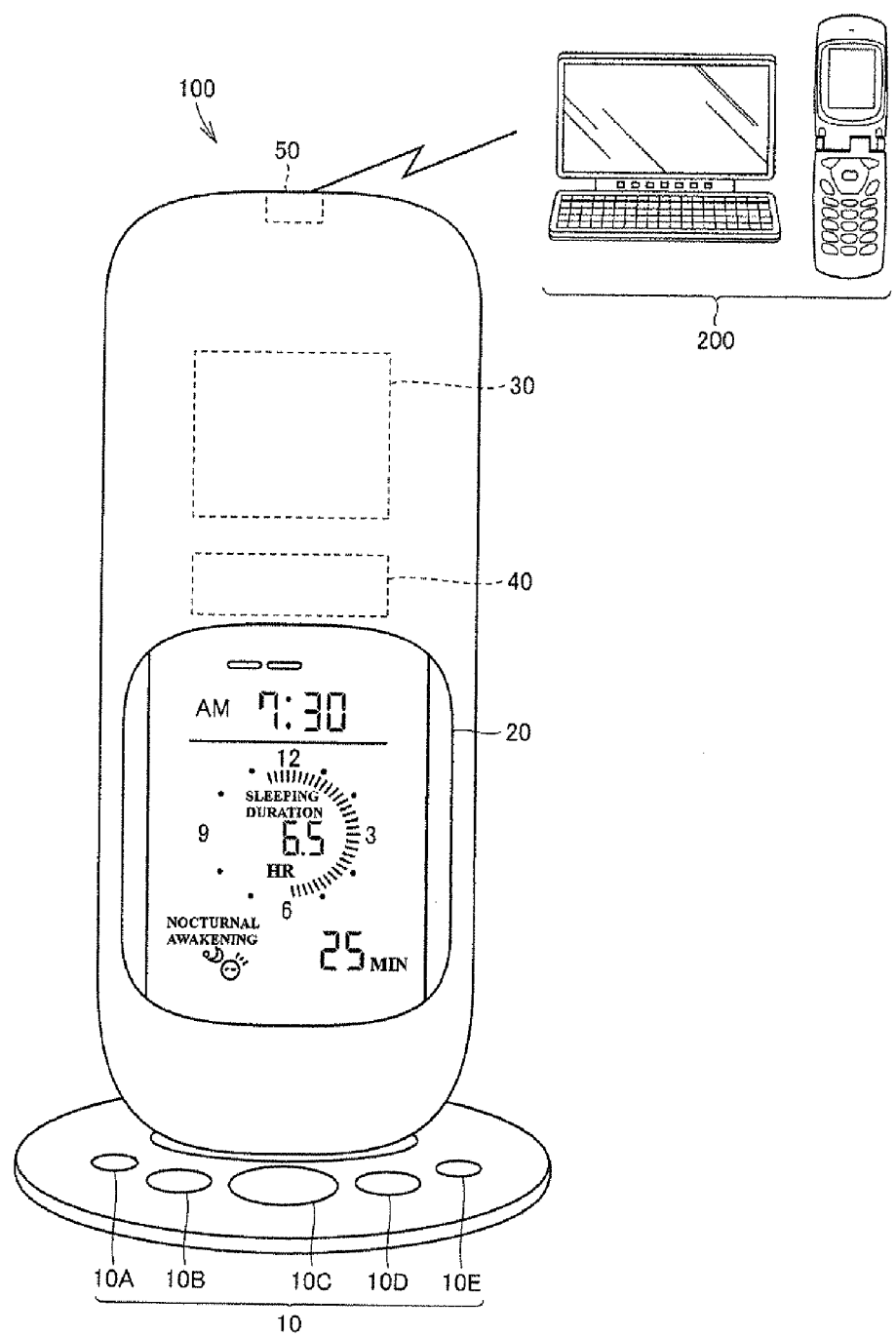
FIG. 1 is a diagram showing a specific example of the external appearance of a sleep evaluation device (hereinafter, abbreviated to "evaluation device") according to an embodiment of the present invention.

FIG. 1 is a diagram showing a specific example of the external appearance of a sleep level evaluation device (hereinafter, abbreviated to "evaluation device") 100 according to the present embodiment. Also, FIG. 2 is a schematic view representing a lateral face of the evaluation device 100, and FIG. 3 is a schematic view of the external appearance seen from diagonally above.

Figure 2:
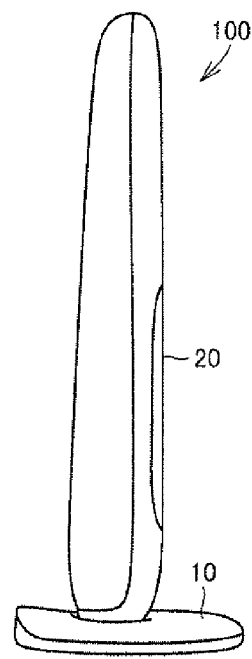
FIG. 2 is a schematic view representing a lateral face of the evaluation device.
Figure 3:
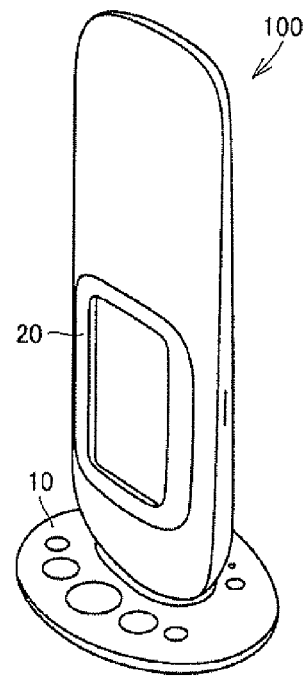
FIG. 3 is the schematic view of the external appearance of the evaluation device seen from diagonally above.

Referring to FIGS. 1 to 3, an evaluation device 100 has, as one example, an external appearance in which a casing that is a rectangular parallelepiped or elongated in shape with rounded corners is placed on a base.

Referring to FIG. 1, an operation button group 10 is disposed on the surface of the base, and a display unit 20 is disposed on the surface of the casing that is placed on the base. Also, a sensor 30 and a control unit 40 are incorporated into the casing.

The button group 10 includes a delete button 10A, a go-to-bed button 10B, a good-night button 10C, a suspension button 10D, and a data processing button 10E. The function of each button will be described later.

In the subsequent description, the surface of the casing on which the display unit 20 is provided will be called the front face of the evaluation device 100.

The evaluation device 100 has a communication unit 50 for performing wireless or wired communication. The communication unit 50 is, as one example, provided at the opposite end of the casing to the base. The evaluation device 100 is connected to a display device 200 such as a personal computer (hereinafter, PC) or a mobile phone, using the communication unit 50, and outputs display data to the display device 200.

Hardware Configuration

Figure 4:
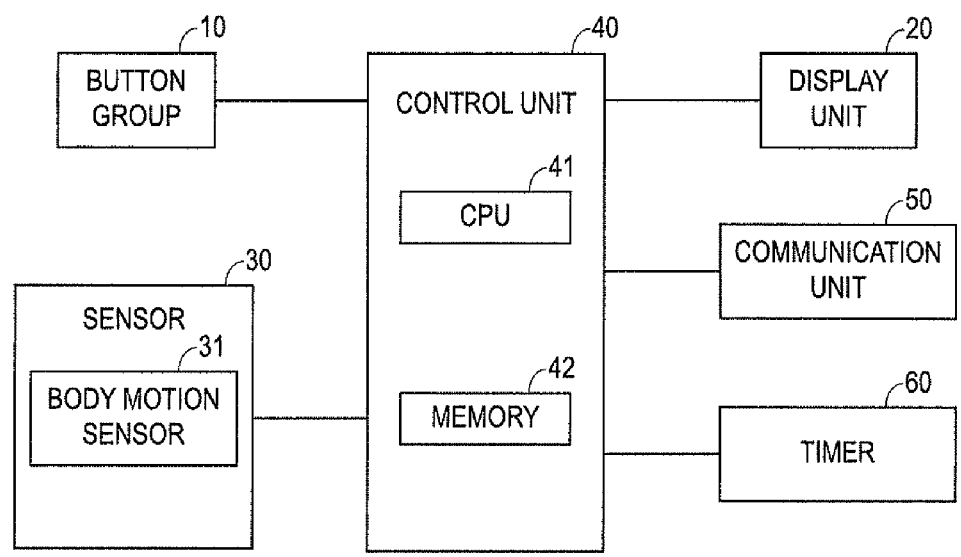
FIG. 4 is a block diagram showing a specific example of the hardware configuration of the evaluation device.

FIG. 4 is a block diagram showing a specific example of the hardware configuration of the evaluation device 100.

Referring to FIG. 4, the button group 10, the sensor 30, the display unit 20 and the communication unit 50 are all connected to the control unit 40.

The button group 10 outputs an operation signal to the control unit 40 as a result of being operated by a person being measured.

The sensor 30 includes a body motion sensor 31 and outputs a sensor signal to the control unit 40. A Doppler sensor is preferably used as the body motion sensor 31. In the subsequent description, the body motion sensor 31 is assumed to be a Doppler sensor. Alternatively, an ultrasonic sensor may be used.

The body motion sensor 31, which is a Doppler sensor, has an output unit (not shown) for outputting radio waves for use in measurement and a receiving unit (not shown). The receiving unit receives radio waves reflected from the surface of a measurement body among radio waves output from the output unit, and outputs a sensor signal that depends on the change in frequency from the output radio waves.

Note that a camera may be provided instead of the body motion sensor 31 as body motion detection means, and body motion may be detected by performing image analysis in the control unit 40.

The control unit 40 includes a CPU 41 for performing overall control, and a memory 42 for storing programs that are executed by the CPU 41, and the like.

The control unit 40 discriminates a sleep level discussed later and generates display data for displaying the sleep level, by the CPU 41 executing a program for performing display stored in the memory 42, and executing an operation using an input operation signal and sensor signal. Also, the control unit 40 executes various processes such as computations of sleep latent duration, which will be described later, and the like.

The control unit 40 executes display control for performing screen display on the display unit 20 based on the display data. Furthermore, communication control for transmitting display data from the communication unit 50 to the display device 200 is executed.

The communication unit 50 may communicate directly with the display device 200, by wireless communication such as infrared communication or communication utilizing Bluetooth (registered trademark), for example, or may have an Internet connection function and communicate with the display device 200 via the Internet.

Furthermore, the communication unit 50 may have a wireless LAN (Local Area Network) server function, and transmit display data discussed below that is expressed in a markup language such as HTML (Hypertext Markup Language), for example, to the display device 200 accessed by a wireless LAN connection.

Also, the evaluation device 100 is provided with a timer 60. The timer 60 is connected to the control unit 40. The CPU 41 acquires time information from the timer 60, specifies time such as go-to-bed time, which will be described later, or the like, and stores the time in the memory 42.

Exemplary Usage

Figure 5:
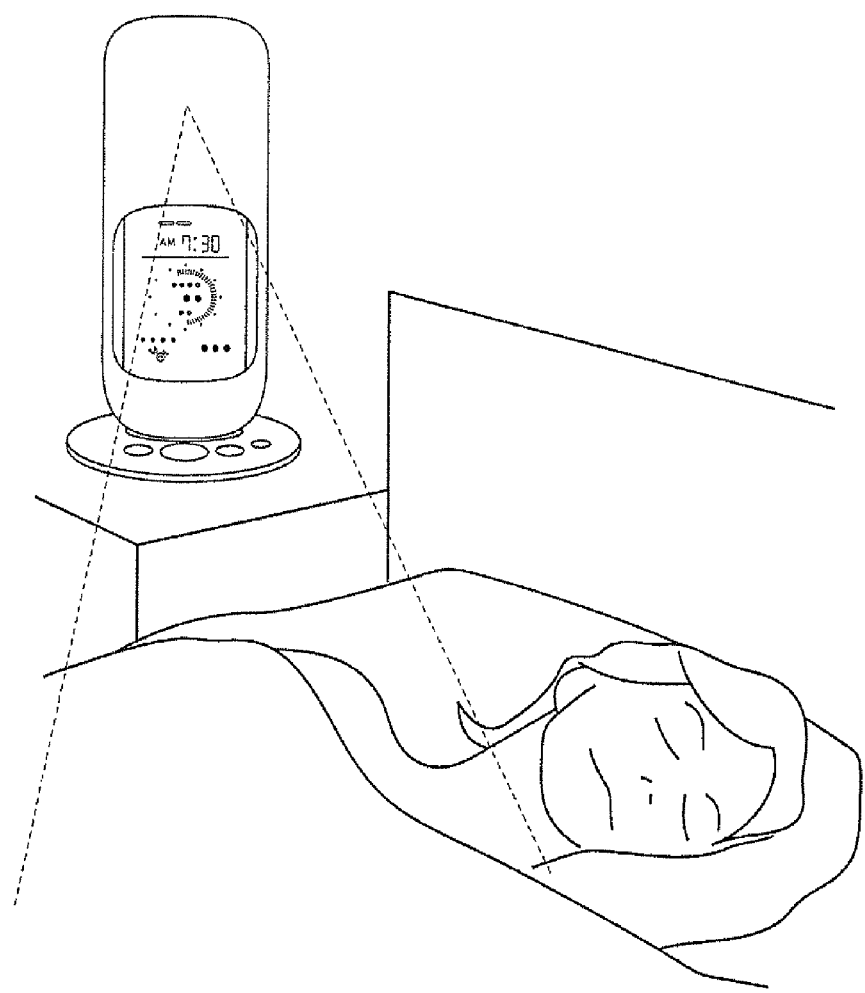
FIG. 5 is a diagram illustrating an exemplary usage of the evaluation device.

FIG. 5 is a diagram illustrating an exemplary usage of the evaluation device 100.

Referring to FIG. 5, the evaluation device 100 is installed in proximity to the person being measured who is asleep (e.g., bedside) as an example. To perform the measurement operation in this state, radio waves are output from the body motion sensor 31 which is a Doppler sensor.

The radio waves output from the body motion sensor 31 reach mainly the vicinity of the chest and shoulders of the person who is sleeping, and the change in frequency of the waves reflected therefrom is output to the control unit 40 as a sensor signal. The control unit 40 detects body motion, such as chest movement of the person who is sleeping or the person rolling over in his or her sleep, based on the change in frequency, and discriminates the sleep level as sleeping state based on those detection results.

Functional Configuration

Figure 6:
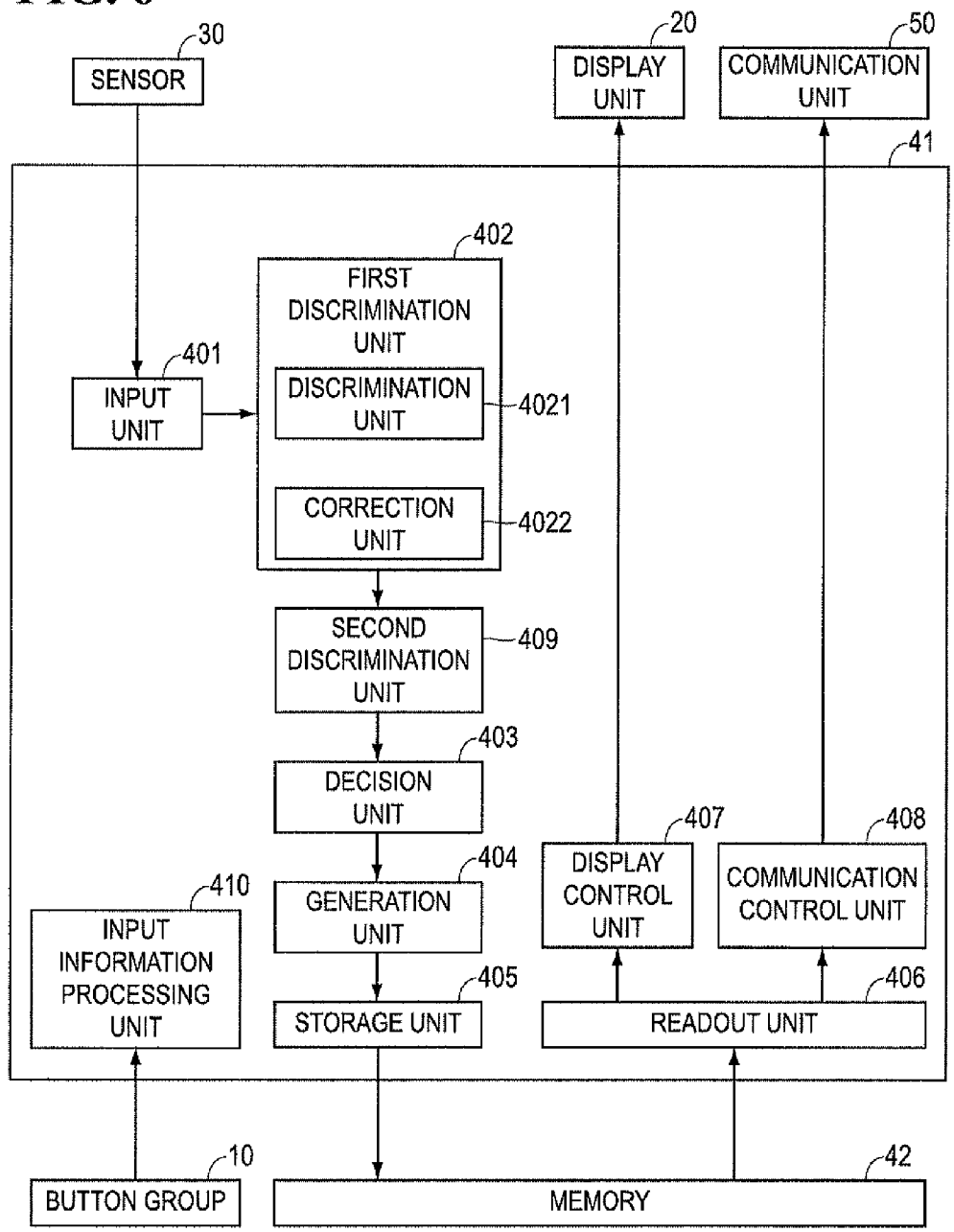
FIG. 6 is a block diagram showing a specific example of the functional configuration for discriminating sleep level in the evaluation device.

FIG. 6 is a block diagram showing a specific example of the functional configuration for discriminating the sleep level in the evaluation device 100. The functions represented in FIG. 6 are mainly formed on the CPU 41 by the CPU 41 executing programs stored in the memory 42, but at least some of the functions may be formed by a hardware configuration such as electrical circuitry.

Referring to FIG. 6, the evaluation device 100 includes an input unit 401 for receiving the sensor signal output from the sensor 30, a first discrimination unit 402 for discriminating the sleeping state of a unit period based on the sensor signal, a second discrimination unit 409 for discriminating a level of the sleeping state in a fixed period consisting of a predetermined number of continuous unit periods, based on a discrimination result for each unit period, a decision unit 403 for deciding a display mode of the fixed period based on the level of the sleeping state, a generation unit 404 for generating display data for displaying the sleep level based on the decided display mode, a storage unit 405 for executing processing for storing display data in the memory 42, a readout unit 406 for reading out display data from the memory 42, a display control unit 407 for executing processing for displaying read display data on the display unit 20, and a communication control unit 408 for executing processing for transmitting display data to the display device 200 using the communication unit 50.

Also, the evaluation device 100 includes an input information processing unit 410 for processing information input from various buttons included in the button group 10.

In the example of FIG. 6, the input unit 401 receives the sensor signal output directly from the sensor 30, but a configuration may be adopted in which the sensor signal is temporarily stored to a predetermined area of the memory 42, and is read out from there by the input unit 401 when performing a display operation.

Sleep Level Discrimination Method

Here, the sleep level discrimination method of the second discrimination unit 409 will be described.

Figure 7:
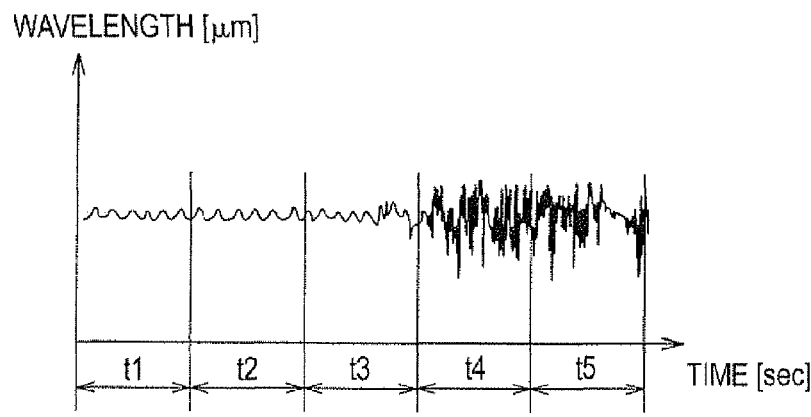
FIG. 7 is a diagram showing a specific example of a sensor signal output from a body motion sensor employing a Doppler sensor.
Figure 8A:
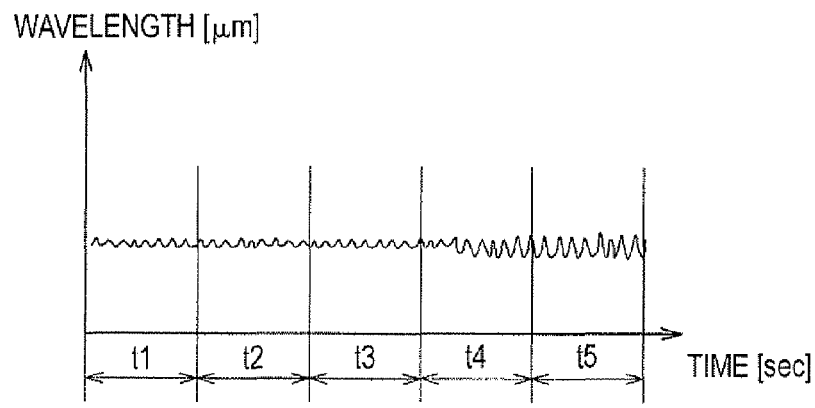
FIG. 8A is a diagram showing a specific example of a respiratory waveform separated from the waveform represented in FIG. 7.
Figure 8B:
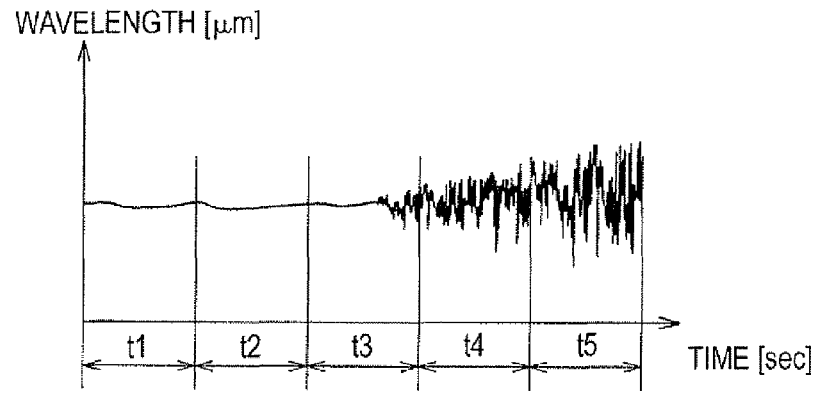
FIG. 8B is a diagram showing a specific example of a body motion waveform separated from the waveform represented in FIG. 7.

FIG. 7 is a diagram showing a specific example of the sensor signal output from the body motion sensor 31 which is a Doppler sensor. FIG. 7 represents the temporal change in the wavelength indicated by a sensor signal that is the frequency change of the wave reflected from the surface of the person being measured.

Referring to FIG. 7, the waveform represented by the sensor signal is a composite wave that includes a waveform representing the body motion (chest movement) of the person being measured that is associated with breathing (hereinafter also called a respiratory waveform) and a waveform representing body motion (body movement) other than breathing such as the person rolling over in his or her sleep or the like (hereinafter also called a body motion waveform).

FIGS. 8A-8B and FIGS. 9A-9C are diagrams showing specific examples of a respiratory waveform and a body motion waveform separated from the waveform represented in FIG. 7.

The respiratory waveform of a person who is in a stable sleeping state has periodicity. Accordingly, in the case where the periodicity of the respiratory waveform is within a predetermined range, that is, when variation in the cycle of the respiratory waveform is within a predetermined range, the person can generally be said to be in a stable sleeping state.

Also, when a person is in a stable sleeping state, there is unlikely to be any body motion other than breathing such as rolling over in his or her sleep. Accordingly, a person can generally be said to be in a stable sleeping state when the amplitude of the body motion waveform is within a predetermined range, and can be said to not be in a stable sleeping state in the case where the amplitude is not within the predetermined range, since there is body motion.

Accordingly, it can be discriminated whether or not the person being measured is in a stable sleeping state with regard to a given period, based on the periodicity of the respiratory waveform or the magnitude of body motion other than breathing in that period. Note that although the sleeping state is discriminated using both the respiratory waveform and the body motion waveform in this example, it is possible to use only one of the waveforms.

As shown in FIG. 6, the first discrimination unit 402 includes a discrimination unit 4021 and a correction unit 4022.

The discrimination unit 4021 separates the waveform that is based on the input sensor signal shown in FIG. 7 into the respiratory waveform and the body motion waveform shown in FIGS. 8A-8B and FIGS. 9A-9C. The discrimination unit 4021 then discriminates whether the person being measured is in a stable sleeping state, every prescribed unit period (periods t1, t2, t3, t4, t5 in FIG. 7), based on the respective waveforms. The unit period here is around 30 seconds to 1 minute, for example. That is, if the variation in the cycle in unit period t1 of the respiratory waveform is less than a preset threshold, it is judged that periodicity is evident in the respiratory waveform in unit period t1. Also, it is judged whether the amplitude in unit period t1 of the body motion waveform is greater than or less than a preset threshold.

The discrimination unit 4021 then discriminates that the sleeping state of the person being measured in unit period t1 is a sleeping state (S), in the case where the respiratory waveform has periodicity in unit period t1, and the amplitude of the body motion waveform is less than the threshold. On the other hand, the discrimination unit 4021 discriminates that the sleeping state of the person being measured in unit period t1 is a waking state (W), in the case where the respiratory waveform does not have periodicity in unit period t1, and the amplitude of the body motion waveform is greater than the threshold. Note that the discrimination unit 4021 may be configured to discriminate that the person being measured is in a waking state if only one of these conditions is satisfied, or in other words, if only the respiratory waveform has periodicity in unit period t1 or the amplitude of the body motion waveform is less than the threshold.

Also, the discrimination unit 4021 may discriminate whether or not the person being measured is present within range of radio waves output from the body motion sensor 31.

Such a discrimination may be performed as follows. For example, the waveform that is based on the sensor signal is separated into the respiratory waveform and the body motion waveform as described above, and then in a case where the amplitude of either the respiratory waveform and the body motion waveform continues to be less than a specific value for a specific time period (30 seconds, for example), the discrimination unit 4021 determines that the person being measured is not present in the above-described range. In another case, the discrimination unit 4021 then determines that the person being measured is present in the above-described range. Note that the discrimination unit 4021 discriminates the state of the person's presence or absence as a state (E) if the person being measured is present, or a state (N) if the person being measured is not present.

FIG. 9A is a diagram showing a specific example of discrimination results of the discrimination unit 4021. As shown in FIG. 9A, the discrimination unit 4021 discriminates whether the person being measured is in a stable sleeping state or a waking state, every unit period of the waveform that is based on the input sensor signal.

However, there may also be unit periods where body motion occurs in a sleeping state or where there is no body motion and breathing is regular in a waking state. Also, there may be cases where a reflected wave from a moving object other than the person being measured is received, resulting in noise occurring in the body motion waveform. In view of this, preferably the correction unit 4022 corrects the discrimination result of such unit periods, according to the discrimination results of adjacent unit periods.

As one example, FIG. 9B shows a specific example of correction of discrimination results shown in FIG. 9A. Referring to FIG. 9A and FIG. 9B, in the case where the number of continuous unit periods having the same discrimination result is less than or equal to a predetermined number, and the number of unit periods continuous therebefore and thereafter having the opposite discrimination result is greater than or equal to a predetermined number, the correction unit 4022 corrects the discrimination result of those continuous unit periods having the same discrimination result to the opposite discrimination result.

Specifically, although the discrimination unit 4021 discriminates that unit period t7 in FIG. 9A is the waking state (W), there are no unit periods discriminated to be the waking state (W) that are continuous with unit period t7 (i.e., number of continuous unit periods is 1), and there is a certain number of unit periods continuous before and after unit period t7 that are discriminated to be the sleeping state (S). The unit period t13 is also in a similar state where the discrimination result is opposite.

If it is assumed that the threshold (first threshold) for the continuous number of discrimination results of the targeted unit period is 2, and the threshold (second threshold) for the continuous number of discrimination results of unit periods before and after the targeted unit period is 2, these conditions are satisfied for unit period t7 in that the one continuous unit period discriminated to be the waking state (W) is less than the first threshold, and the three continuous unit periods before and after unit period t7 that have the opposite discrimination result are greater in number than the second threshold. Accordingly, the correction unit 4022 corrects the discrimination result of unit period t7 to the sleeping state (S) which is the opposite discrimination result.

Similarly, the correction unit 4022 also corrects the discrimination result of unit period t13 to the waking state (W) which is the opposite discrimination result.

Next, the second discrimination unit 409 discriminates the sleep level for a fixed period consisting of continuous unit periods, based on the discrimination result of each unit period. The unit period here is around 5 minutes to 10 minutes, for example.

Here, the sleep levels denote levels of the sleeping depth defined in terms of the regularity of breathing and the existence and continuity of body motion. Specific examples include:

Level 1: Sleeping state with no body motion and regular breathing;
Level 2: Sleeping state with one-off body motion;
Level 3: Sleeping state with continuous body motion;
Level 4: Waking state with continuous body motion that is ongoing; and
Level 5: Full waking state.

Figure 13:
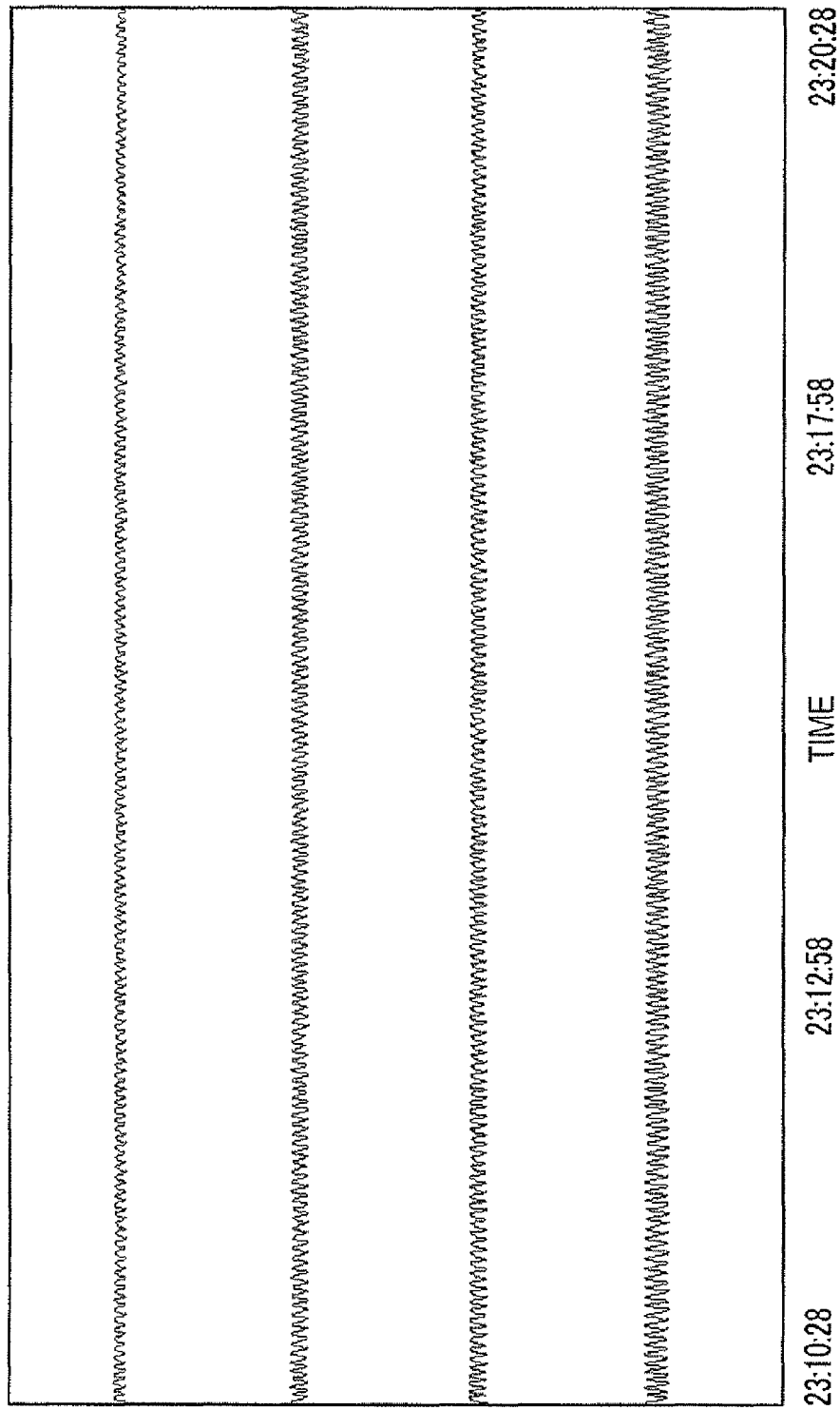
FIG. 13 is a diagram showing specific examples of typical waveforms of a sensor signal that correspond to a sleep level.
Figure 14:
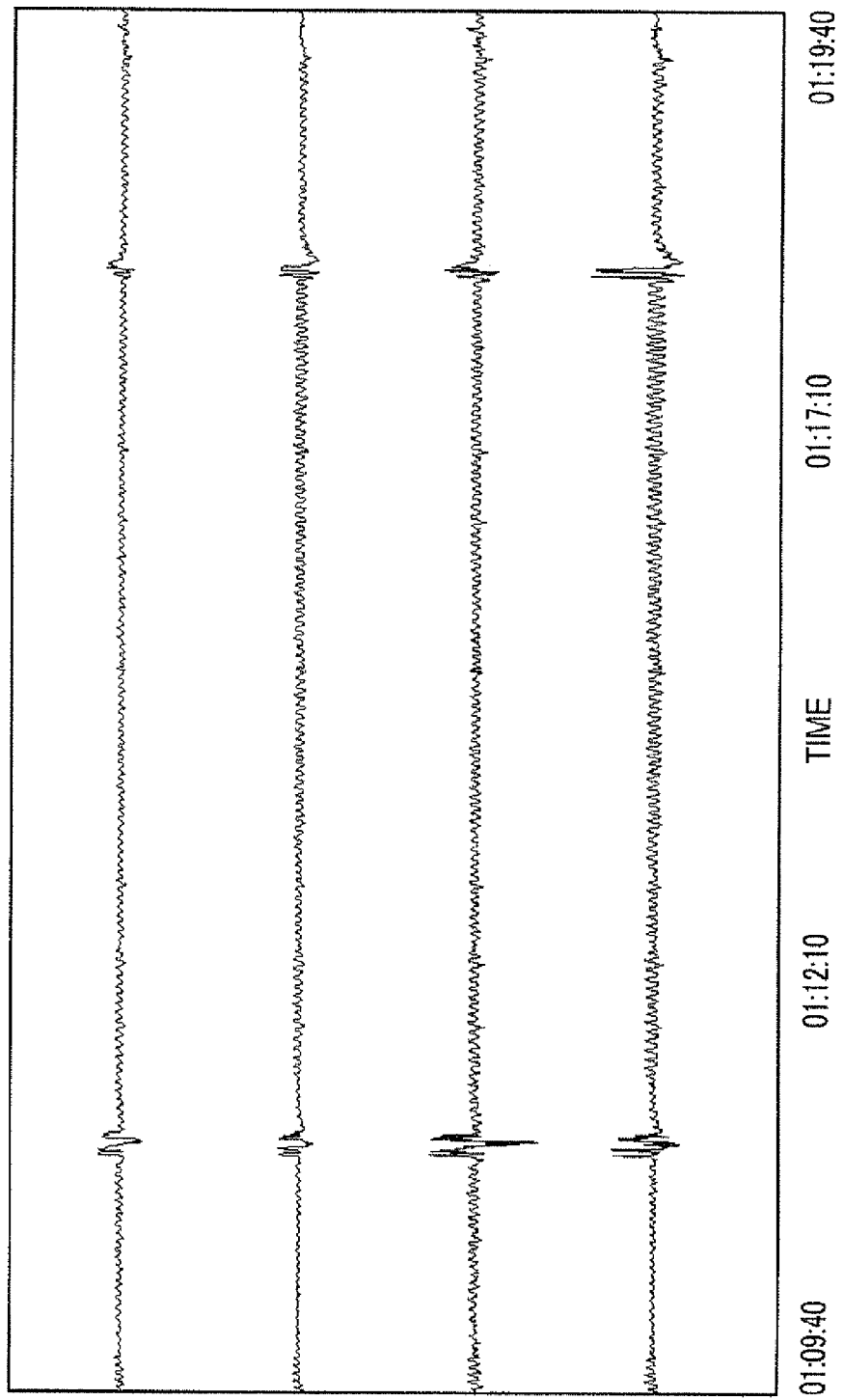
FIG. 14 is a diagram showing specific examples of typical waveforms of a sensor signal that correspond to a sleep level.
Figure 15:
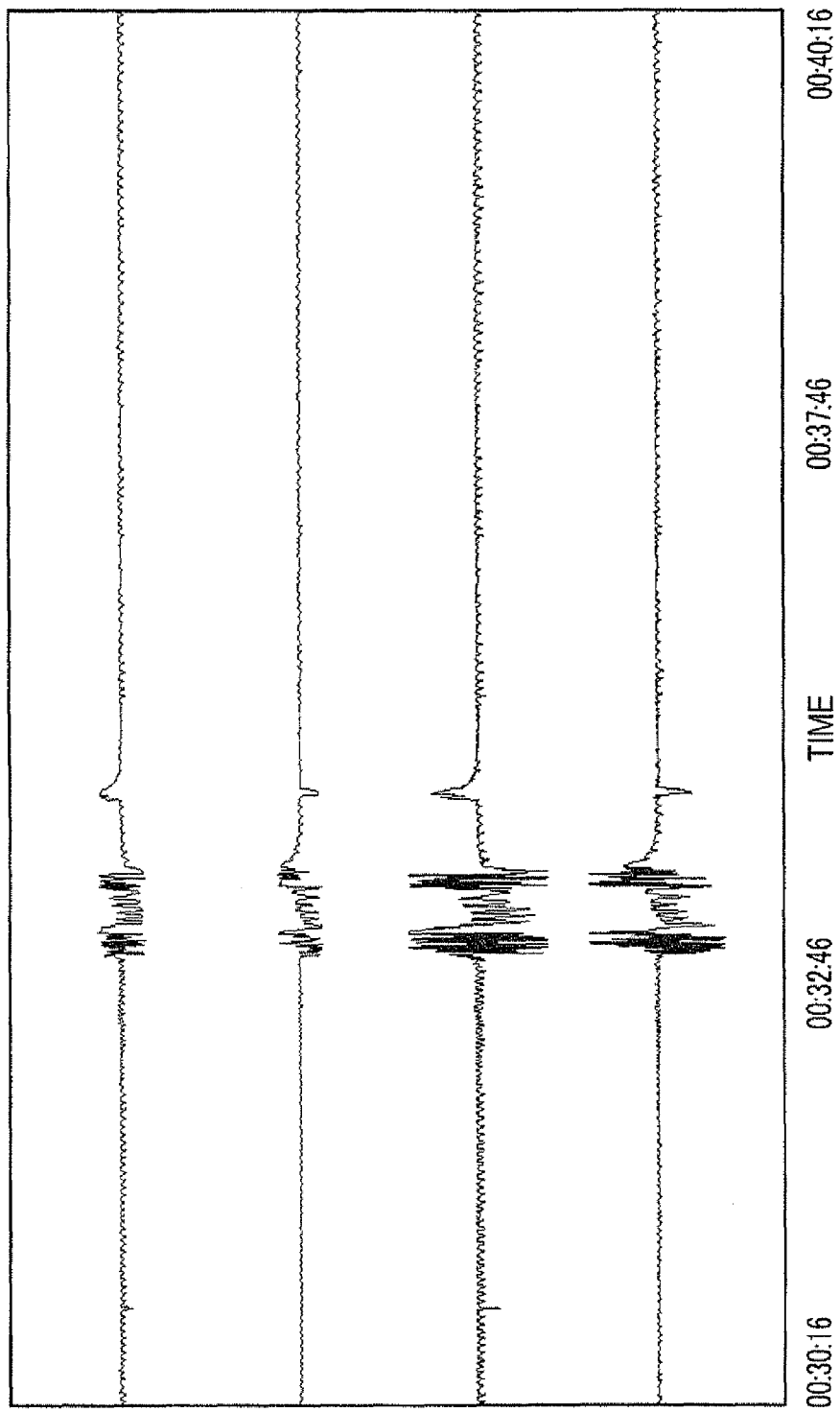
FIG. 15 is a diagram showing specific examples of typical waveforms of a sensor signal that correspond to a sleep level.
Figure 16:
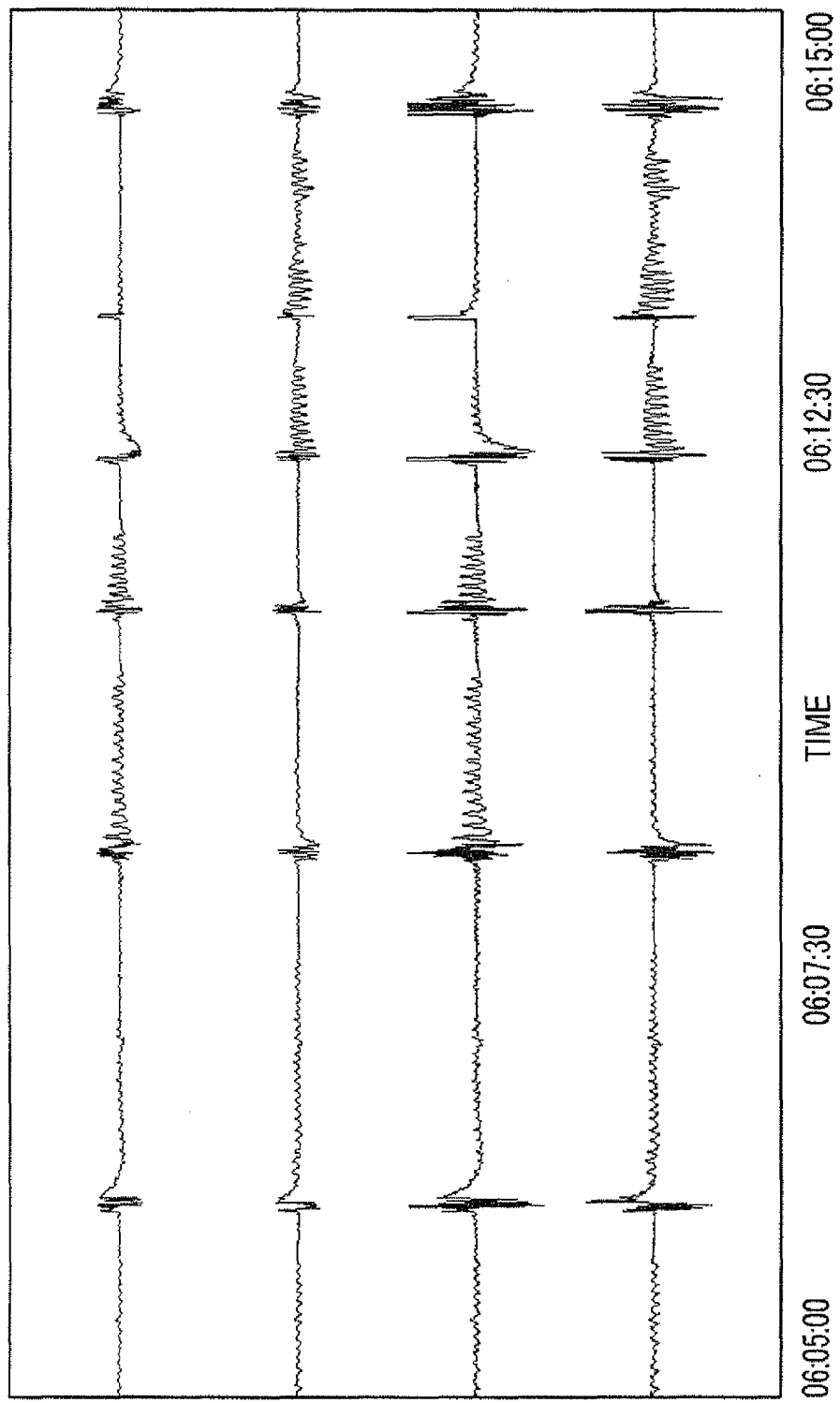
FIG. 16 is a diagram showing specific examples of typical waveforms of a sensor signal that correspond to a sleep level.
Figure 17:
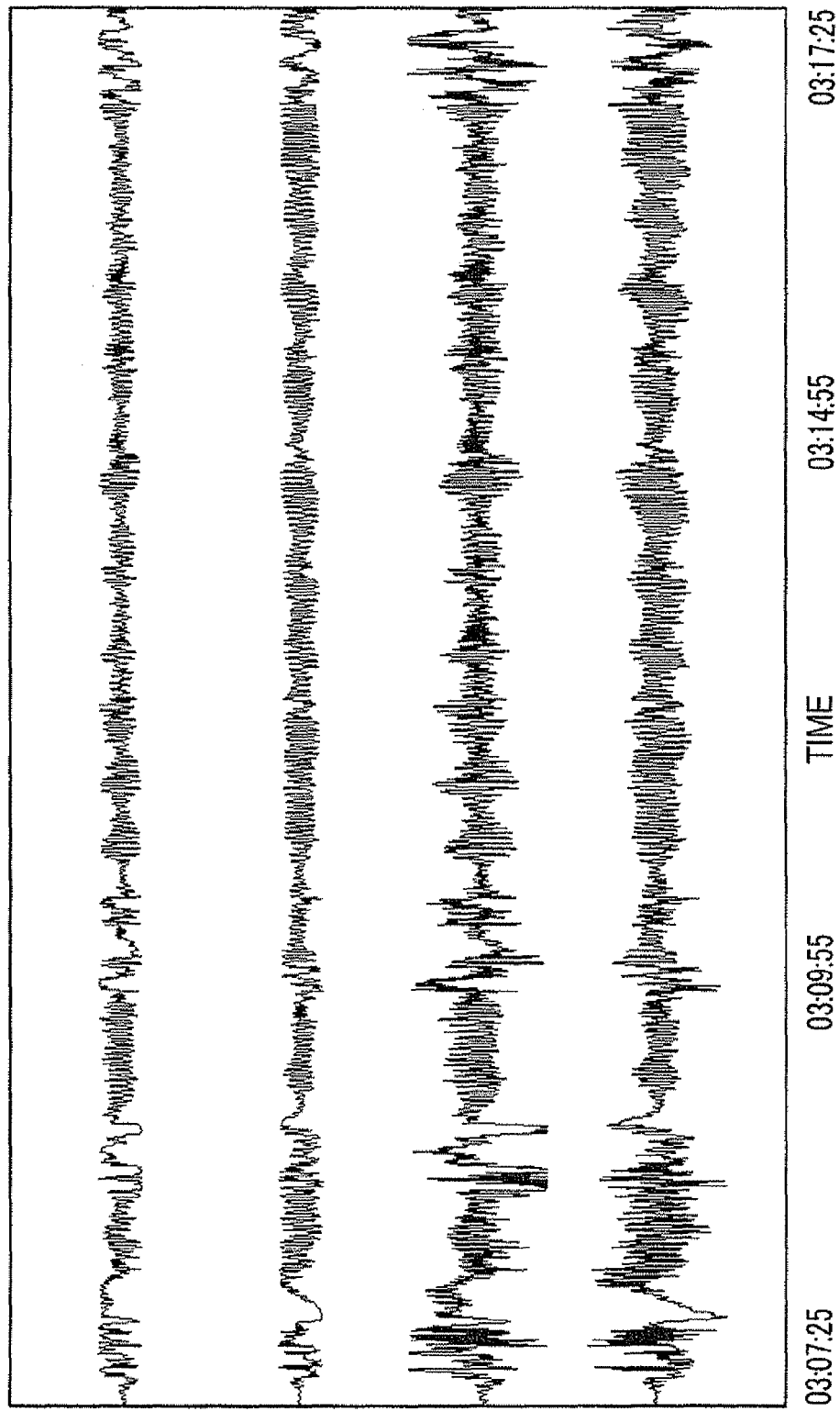
FIG. 17 is a diagram showing specific examples of typical waveforms of a sensor signal that correspond to a sleep level.
Figure 18:
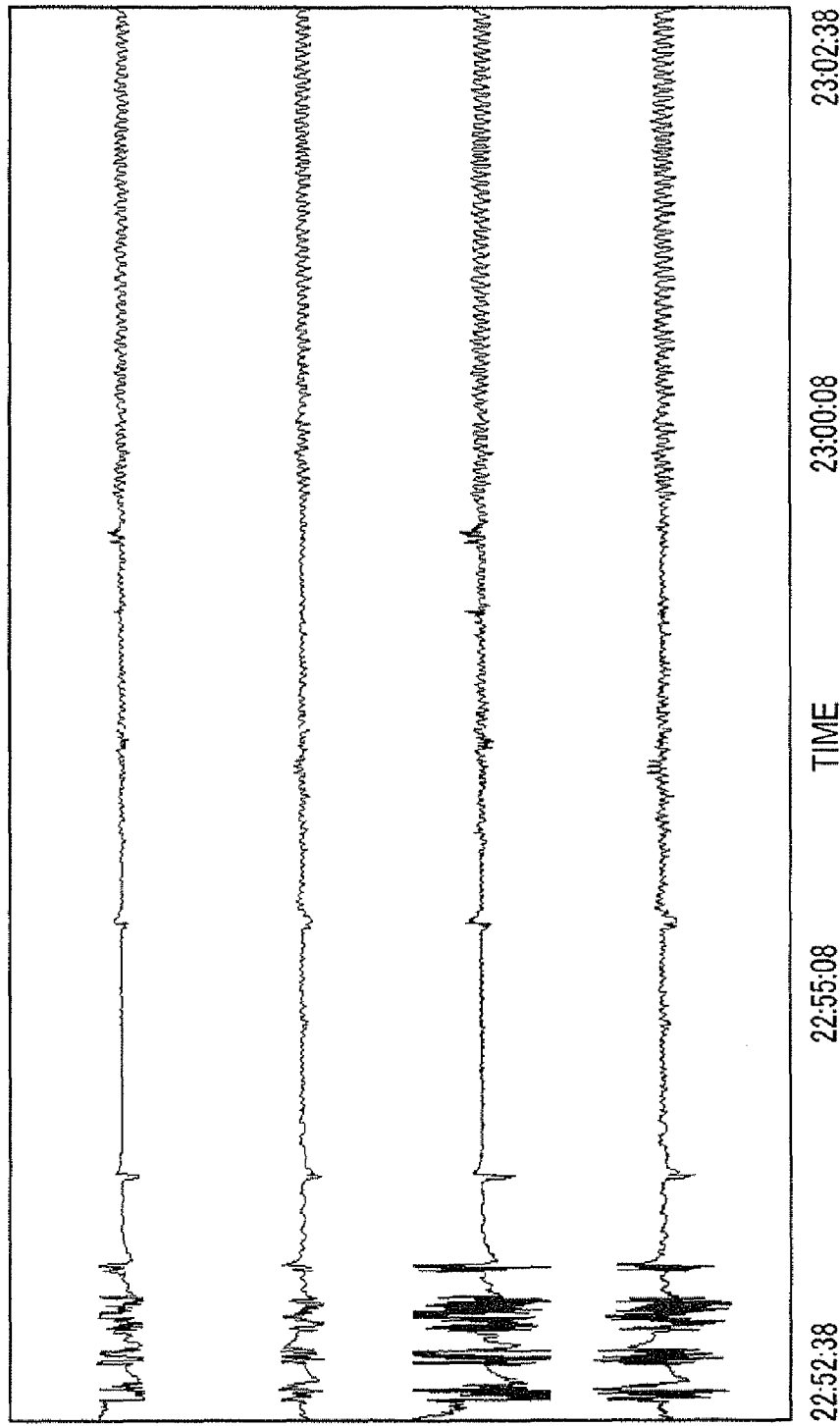
FIG. 18 is a diagram showing specific examples of typical waveforms of a sensor signal that correspond to a sleep level.
Figure 19:
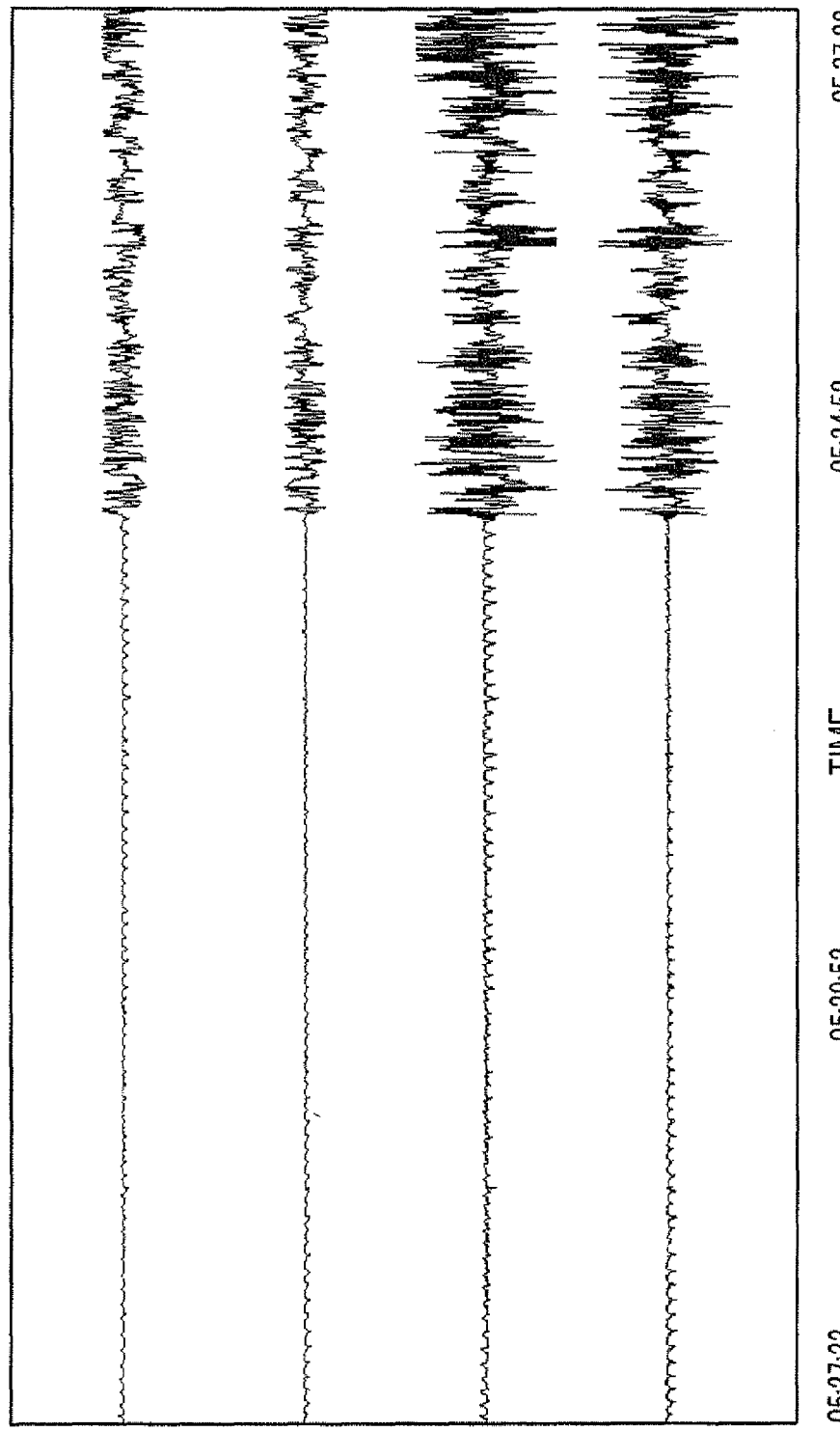
FIG. 19 is a diagram showing specific examples of typical waveforms of a sensor signal that correspond to a sleep level.

The second discrimination unit 409 stores, as a discrimination value for each level, a continuous number and a ratio of discrimination results of the unit periods constituting a fixed period. As an example, FIG. 13 represents specific examples of typical waveforms of the sensor signal in the case of the above level 1, FIG. 14 represents specific examples of typical waveforms of the sensor signal in the case of the above level 2, FIG. 15 and FIG. 16 represent specific examples of typical waveforms of the sensor signal in the case of the above level 3, FIG. 17 represents specific examples of typical waveforms of the sensor signal in the case of the above level 4, FIG. 18 represents typical waveforms of the sensor signal in the case of the above level 5, particularly waveforms of the sensor signal when the person being measured is going to bed, and FIG. 19 represents typical waveforms of the sensor signal in the case of the above level 5, particularly waveforms of the sensor signal when the person being measured is waking up. The second discrimination unit 409 prestores, as a discrimination value for each level, a continuous number and a ratio of discrimination results represented in the waveforms of these sensor signals. FIG. 9C is a diagram representing a specific example of the sleep level discrimination result for each fixed period. That is, referring to FIG. 9B and FIG. 9C, the second discrimination unit 409 discriminates the sleep level for each fixed period, by comparing the continuous number of the discrimination result with the stored discrimination value, and comparing the ratio of the discrimination results with the discrimination value, for the continuous unit periods constituting the fixed period.

Display Examples of Sleep Level

With regard to a given time slot, the evaluation device 100 sets, every fixed period belonging to that time slot, segments representing the fixed period to a display mode that depends on the sleep level, and displays the segments in chronological order.

FIG. 10 is a diagram showing a first specific example of the display of sleep levels.

Referring to FIG. 10, as the first example, an example is shown in which segments representing each fixed period are arranged in chronological order, and the respective segments are displayed with colors that depend on the sleep level of the fixed period. Note that, in FIG. 10, the display colors that depend on sleep level are expressed using different types of hatching, for convenience of display. The same applies to a second display example discussed later.

In order to perform display according to the first example, the decision unit 403 prestores display colors that depend on sleep level, and decides the display color according to the discriminated sleep level, every fixed period. The generation unit 404 then generates display data for setting the segments corresponding to that fixed period to the decided display color.

As a result of display processing based on this display data being performed by the display control unit 407 or being performed by the display device 200 to which the display data has been transmitted by the communication unit 50 under the control of the communication control unit 408, display as shown in FIG. 10 is realized on a display unit thereof.

In FIG. 10, every fixed period belonging to time slots of one day, for example, the sleep level of the person being measured for that fixed period is displayed with a corresponding color. Thus, the user is able to grasp at a glance the transition in the sleep level of the person being measured for each fixed period in any given time slot.

Here, "user" may be the same person as a person being measured, or may be a different person from a person being measured such as a doctor who analyses information relating to sleep of the person being measured or the like.

Furthermore, in order to display a display screen such as shown in FIG. 10, preferably the generation unit 404 generates display data that represents the segments representing each fixed period, over two or more consecutive days arranged by day on the same time axis. The user is thereby able to easily compare the transition in the sleep level of the person being measured for each fixed period in any given time slot over consecutive days. The same applies to the second display example discussed later.

Note that although an example is represented in FIG. 10 in which measurement results for consecutive days such as one week, for example, are displayed adjoining one another, display is not limited to consecutive days, and a configuration may be adopted in which the measurement results for a specific day such as Monday, for example, are displayed adjoining one another. The same applies to the second display example discussed later.

Figure 11:
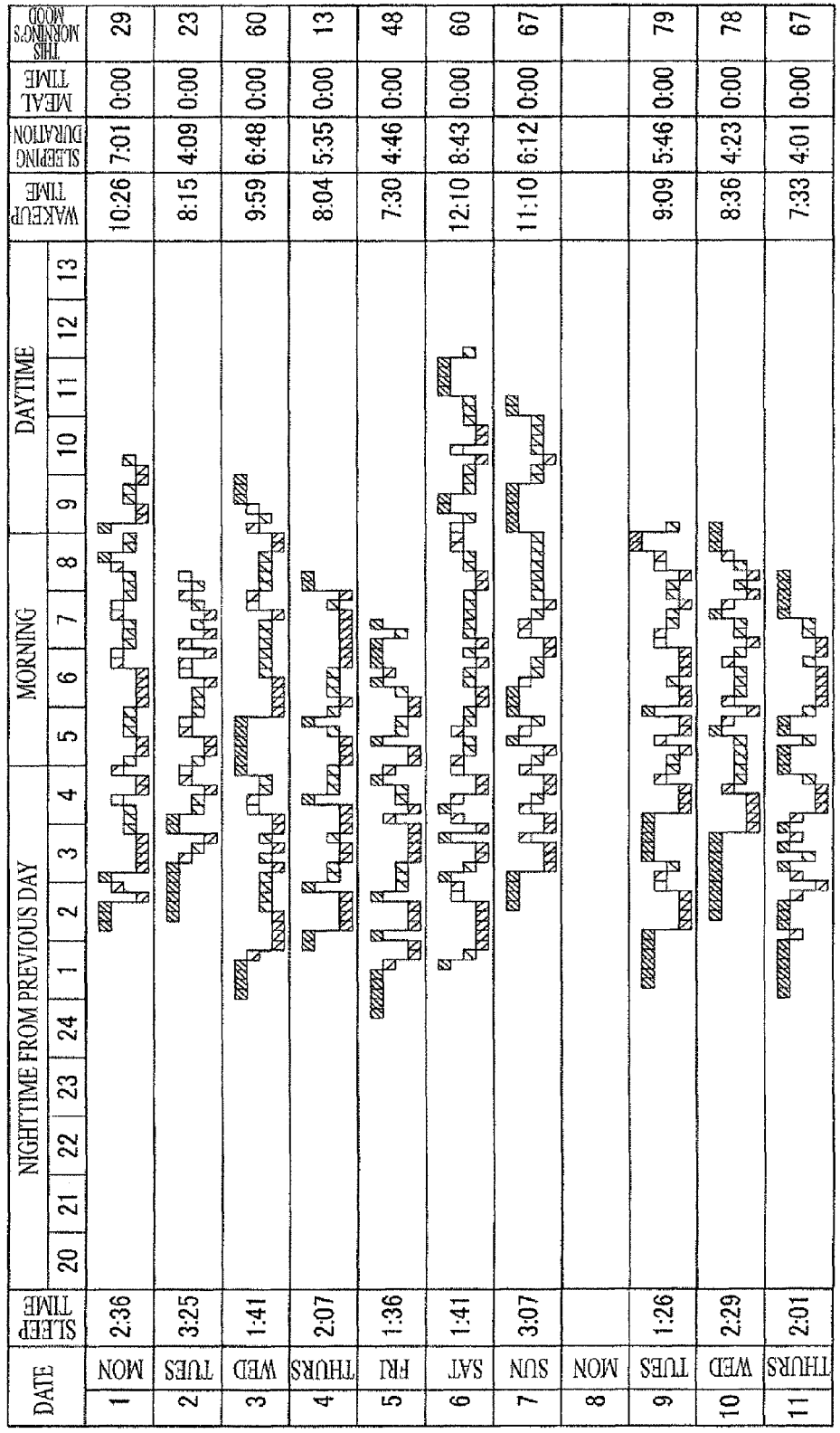
FIG. 11 is a diagram showing a second specific example of the display of sleep levels.

FIG. 11 is a diagram showing a second specific example of the display of sleep levels.

Referring to FIG. 11, as the second example, an example is shown in which segments representing each fixed period are arranged in chronological order, and, furthermore, an axis representing the sleep levels is set in a direction orthogonal to the time axis, and the respective segments are displayed at least in positions that depend on the sleep level. More preferably, as shown in FIG. 11, each segment is, furthermore, also represented with a color that depends on the sleep level of the fixed period.

In order to perform display according to the second example, the display position of the segments on the axis representing sleep level is decided. The generation unit 404 then generates display data for setting the segments corresponding to that fixed period to the decided display positions. In the case of deciding the display color together with the display position, the display color is decided similarly to the first example.

As a result of display processing based on this display data being performed by the display control unit 407 or being performed by the display device 200 to which the display data has been transmitted by the communication unit 50 under the control of the communication control unit 408, display such as shown in FIG. 11 is realized on a display unit thereof.

In FIG. 11, every fixed period belonging to time slots of one day, for example, the segments representing that fixed period are displayed, relative to the axis indicating sleep level that is orthogonal to the time axis, in positions that depend on the sleep level of the person being measured. Thus, the user is able to intuitively grasp at a glance the transition in the sleep levels of the person being measured for each fixed period in any given time slot.

Note that in the examples in FIG. 10 and FIG. 11, display that is expressed with segments every fixed period and in which the segments are arranged in chronological order is performed. However, the present invention is not limited to display using segments, and other forms of display may be performed, such as display in which an entire time slot specified in advance is converted to a bar graph and corresponding times are set to display colors that depend on sleep level, Operation Outline As described with reference to FIG. 5, the evaluation device 100 detects body motion of a person being measured who is asleep on bedding ("bed" is shown as an example in FIG. 5), and discriminates the sleep level of the person being measured based on the detected movement. The discrimination result is then displayed on a display device, as shown in FIG. 10 or 11.

Here, there is a case where the person being measured does not necessarily intend to go to sleep immediately after moving onto the bedding. For example, the person being measured may intend to perform an activity such as reading or the like for a predetermined time after moving onto the bedding and then to go to sleep. Herein, activities other than sleep after moving onto the bedding such as "reading" described above and the like are referred to as "pre-sleep activity". Moreover, the evaluation device 100 is capable of managing and displaying information including a pre-sleep activity, for a period from when the person being measured moves onto bedding to when he/she falls asleep.

Hereinafter, the operation of the evaluation device 100 for managing information including sleep will be described.

With the evaluation device 100, the person being measured operates the go-to-bed button 10B immediately after moving onto bedding. Also, the person being measured inputs the type of pre-sleep activity into the evaluation device 100. Also, the person being measured operates the good-night button 10C at a timing at which he/she intends to go to sleep, after moving onto the bedding, or after performing a pre-sleep activity. In other words, the person being measured operates the good-night button 10C at the point in time when he/she thinks that "it's time to sleep" after moving onto the bedding, or after performing a pre-sleep activity such as reading or the like.

The CPU 41 stores in the memory 42 the time when the go-to-bed button 10B is operated (go-to-bed time), and the time when the good-night button 10C is operated (measurement start time) for each sleeping period. "Sleeping period" will be described later.

Also, with the evaluation device 100, the person being measured again operates the good-night button 10C when waking up. The CPU 41 stores in the memory 42 the time when the good-night button 10C again is operated (measurement end time) for each sleeping period.

In the present embodiment, a period from when the good-night button 10C is first operated to when the good-night button 10C again is operated, that is, a period from measurement start time to measurement end time is referred to as "sleeping period".

Table 1 is a diagram schematically showing an example of information stored to perform display relating to pre-sleep activity for each sleeping period.

TABLE 1

| ITEM | CONTENT |
| --- | --- |
| Go-to-bed time | 20110101/22:00 |
| Measurement start time | 20110101/23:00 |
| Measurement end time | 20110102/6:00 |
| Level 3 reaching time | 20110101/23:45 |
| Sleep latent duration | 0:45 |
| Pre-sleep duration | 1:00 |
| Pre-sleep activity type information | yoga |

Referring to Table 1, the memory 42 stores go-to-bed time, measurement start time, and measurement end time. Note that with regard to each time, the number before "/" represents year, month and day, and the number after "/" represents time.

Also, the CPU 41 stores in the memory 42, as level 3 reaching time, the time when a sleep level reaches "level 3" for the first time in each sleeping period. With regard to level 3 reaching time, the number before "/" represents year, month and day, and the number after "/" represents time.

The CPU 41 then computes the time required from measurement start time to level 3 reaching time, and stores the computed duration as sleep latent duration in the memory 42.

Also, the CPU 41 computes the time required from go-to-bed time to measurement start time, and stores the computed duration as pre-sleep duration in the memory 42.

Furthermore, as a result of receiving operations performed on the button group 10 and the like for each sleeping period, the CPU 41 receives information specifying the type of pre-sleep activity and stores the received input as pre-sleep activity type information in the memory 42.

Display of Pre-Sleep Information

The CPU 41 causes the display device to display pre-sleep duration and sleep latent duration along with the type of pre-sleep activity for each sleeping period, based on the information described with reference to Table 1. FIG. 12 is a diagram showing an example of screens to be displayed in such a manner.

As shown in FIG. 12, the type of pre-sleep activity (yoga, reading, or the like), pre-sleep duration, and sleep latent duration are associated and stored for each sleeping period. Note that in the display of FIG. 12, "date" refers to the day to which the measurement start time belongs.

Because of the display shown in FIG. 12, the person being measured can easily understand the relationship between a pre-sleep activity and sleep latent duration and the relationship between pre-sleep duration and sleep latent duration, and can select his/her own activity (for example, type of pre-sleep activity) so as to have sleep in an ideal mode.

Note that either one of the type of pre-sleep activity and pre-sleep duration needs only be displayed along with sleep latent duration.

Operation Flow of Sleep Discrimination Processing

Figure 21:
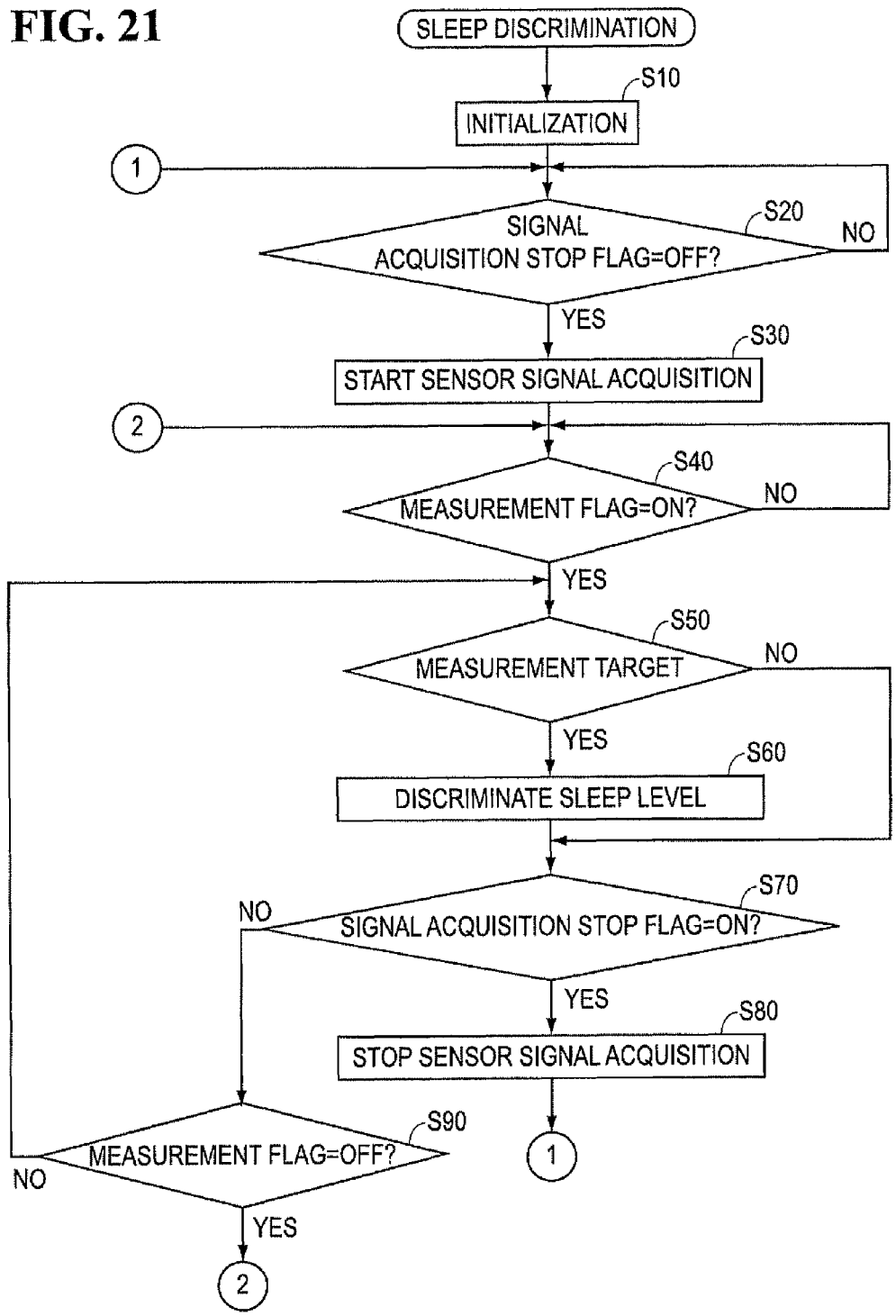
FIG. 21 is a flowchart of sleep discrimination processing.

FIG. 21 is a flowchart of processing for discriminating a sleeping state (sleep discrimination processing) of a person being measured in the evaluation device 100. The processing is started when the evaluation device 100 is turned on, for example. Note that the operation of the processing is realized by the CPU 41 reading out and executing a program for display stored in the memory 42 so as to cause the functions shown in FIG. 6 to work.

In the sleeping discrimination processing, the CPU 41 sets various flags to ON or OFF, such as a measurement flag, a signal acquisition stop flag, and the like. In the initial state of the evaluation device 100, the states of the measurement flag and the signal acquisition stop flag are set to OFF. The function of each flag will be described later.

Referring to FIG. 21, when the evaluation device 100 is turned on, the CPU 41 initializes the evaluation device 100 in step S10, and advances the processing to step S20.

The CPU 41 determines whether or not the state of the signal acquisition stop flag is OFF in step S20, and advances the processing to step S30 if it is determined to be OFF. On the other hand, if the state of the signal acquisition stop flag is ON, then the CPU 41 waits in step S20 until it is set to OFF.

The CPU 41 starts acquisition of a sensor signal using the body motion sensor 31 in step S30, and advances the processing to step S40.

The CPU 41 determines whether or not the state of the measurement flag is ON in step S40, and advances the processing to step S50 if it is determined to be ON. Note that if the state of the measurement flag is OFF, then the CPU 41 waits in step S40 until it is set to ON.

In step S50, the CPU 41 discriminates whether or not a target to be measured is present in a range within which the body motion sensor 31 detects the target; in other words, whether or not the person being measured is present within range of the radio waves output from the body motion sensor 31. This discrimination can be realized based on whether or not the amplitude of either the respiratory waveform or the body motion waveform after the signal output from the motion sensor 31 is separated into the respiratory waveform and the body motion waveform continues to be smaller than a specific value for a specific time period (for example, 30 seconds). In the case where it is determined that the person being measured is present, in other words, in the case where it is discriminated that the state of the person's presence or absence is the state (E), the CPU 41 advances the processing to step S60. Note that in the case where it is determined that the person being measured is not present, in other words, in the case where it is discriminated that the state of the person's presence or absence is the state (N), the CPU 41 advances the processing to step S70 without performing the process of step S60.

The CPU 41 discriminates the sleep level in step S60, and advances the processing to step S70. Note that in step S60, for example, the CPU 41 discriminates the sleeping state in each preset unit period, based on the periodicity of the respiratory waveform and/or the magnitude of the amplitude of the body motion waveform obtained in step S50 for each preset unit period. Furthermore, the discrimination results are corrected according to the discrimination results of the adjacent unit periods. Moreover, with respect to a fixed period consisting of the above-described successive unit periods, the sleep level is discriminated based on the discrimination result of each unit period. The obtained sleep level is then stored in the memory 42 along with time information corresponding to the sleep level.

The CPU 41 determines whether or not the state of the signal acquisition stop flag is ON in step S70, and advances the processing to step S80 if it is determined to be ON. On the other hand, if it is determined to be OFF, the CPU 41 advances the processing to step S90.

The CPU 41 stops acquisition of a sensor signal using the body motion sensor 31 in step S80, and returns the processing to step S20.

The CPU 41 determines whether or not the state of the measurement flag is OFF in step S90, and returns the processing to step S40 if it is determined to be OFF. On the other hand, if it is determined to be ON, the CPU 41 advances the processing to step S50.

In the sleep discrimination processing described above, a sensor signal is acquired using the body motion sensor 31 (steps S20, S30, S70, and S80) on the condition that the state of the signal acquisition stop flag is OFF. In the case where the state of the flag is ON, the sensor signal is not acquired. Note that it is preferable that the body motion sensor 31 is controlled so as to output radio waves for measurement, for example, only while sensor signals are being acquired.

Also, in the sleep discrimination processing, sleep level is discriminated (steps S40, S60, and S90) on the condition that the state of the measurement flag is ON. In the case where the state of the flag is OFF, sleep level is not discriminated.

Operation Flow of Button Operation Processing

Figure 22:
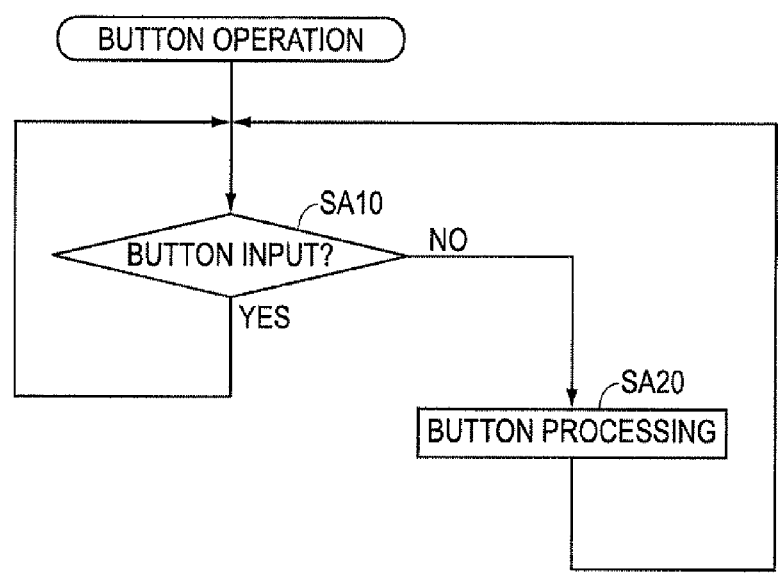
FIG. 22 is a flowchart of button operation processing.

In the evaluation device 100, operations being performed on various buttons constituting the button group 10 are received along with various processes such as sleep discrimination processing and the like. FIG. 22 is a flowchart of processing for operating (button operation processing) in correspondence with the operations performed on the button group 10. Hereinafter, the content of the processing will be described with reference to FIG. 22.

In the button operation processing, the CPU 41 first determines whether or not an operation is performed on any button of the button group 10 in step SA10, and if it is determined that an operation is performed, the CPU 41 advances the processing to step SA20.

In step SA20, the CPU 41 executes the content of processing corresponding to the type of the button operated, and returns the processing to step SA10.

Here, the content of processing for each button that is executed in step SA20 will be described.

In the case where the operated button is the go-to-bed button 10B, the CPU 41 stores measurement time of the timer 60 at this point in time as the go-to-bed time in the memory 42.

In the case where the operated button is the good-night button 10C, the CPU 41 switches the state of the measurement flag between ON and OFF. In other words, if the good-night button 10C is operated when the state of the flag is ON, the CPU 41 sets the state of the flag to OFF. On the other hand, if the good-night button 10C is operated when the state of the flag is OFF, the CPU 41 sets the state of the flag to ON.

In the case where the operated button is the data processing button 10E, the CPU 41 receives the information specifying the type of pre-sleep activity. In this case, for example, candidates for the type of pre-sleep activity stored in the memory 42 in advance are displayed on the display unit 20 in response to the data processing button 10E being operated.

Examples of candidates include, for example, "reading", "listening to music", "stretching", "yoga", and "other". The CPU 41 then receives information specifying the type of pre-sleep activity among the candidates, based on the operation performed on various buttons included in the button group 10.

In the case where the operated button is the delete button 10A, the CPU 41 deletes stored data of a signal waveform corresponding to a period from the point in time when the state of the measurement flag was previously set to OFF to the point in time when the delete button 10A was operated, among the signal waveforms stored in the memory 42 and output from the body motion sensor 31.

In the case where the operated button is the suspension button 10D, similarly to the delete button 10A being operated, the CPU 41 deletes stored data of a signal waveform corresponding to the point in time when the state of the measurement flag was set to OFF to the point in time when the suspension button 10D was operated, among the signal waveforms in the memory 42.

Summary of Operation Flow

In the evaluation device 100, the processing of button operation is executed along with the sleep discrimination processing.

Accordingly, discrimination of sleep level is started (steps S40 to S60) in response to a first operation being performed on the good-night button 10C. The discrimination of sleep level then ends (steps S90 and S40) in response to a second operation being performed on the good-night button 10C. The sleeping period ends as a result of the second operation being performed on the good-night button 10C. Therefore, in the case where the good-night button 10C is further operated, the operation is dealt with as a first operation.

Also, in the evaluation device 100, when the delete button 10A is operated, stored data of the signal waveform detected by the body motion sensor 31 is deleted from when the latest sleeping period ended to the point in time when the operation was performed. Note that it is assumed that in the evaluation device 100, from when acquisition of a signal waveform to be detected by the body motion sensor 31 is started in step S30 to when acquisition of a signal is stopped in step S80, the acquired waveform is stored in the memory 42. In addition, as a result of processing for deleting stored data being executed for the operation performed on the delete button 10A as described above, the person being measured can delete stored data of the signal waveform for a period for which the person being measured does not desire to leave the stored data in the evaluation device 100 through the operation performed on his/her own will.

Furthermore, in the evaluation device 100, when the suspension button 10D is operated, the stored data of the signal waveform detected by the body motion sensor 31 from when the latest sleeping period ended to the point in time when the operation was performed is deleted, and the detection of signals performed by the body motion sensor 31 is also stopped (step S80). In this case, the detection of signals performed by the body motion sensor 31 is not resumed until the state of the signal acquisition stop flag is set to OFF by the suspension button 10D being operated again (YES in step S20), or until the state of the flag is set to OFF by the evaluation device 100 being initialized (step S10).

Effects of Embodiments

As a result of the above-described operations being performed in the evaluation device 100, a situation in which periods other than the period that the person being measured desires to evaluate are evaluated can be avoided as much as possible, and thus the accuracy in evaluations of sleeping states performed by the sleep evaluation device can be improved.

Also, as described above, in the evaluation device 100, the CPU 41 executes control with regard to discrimination of sleep level and detection of signals performed by the body motion sensor 31, based on operations performed on various buttons included in the button group 10.

Figure 20:
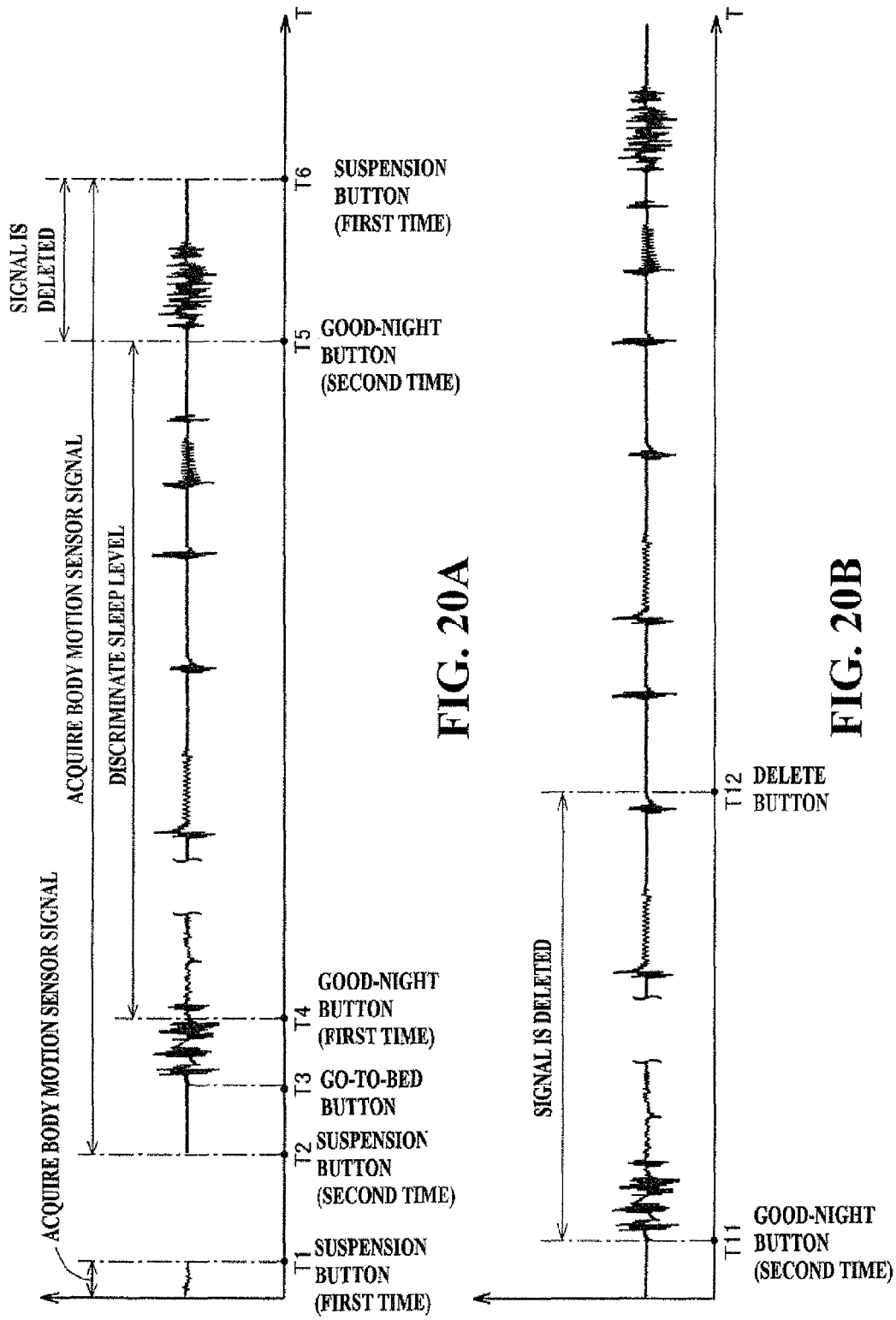
FIG. 20 is a diagram for illustrating the content of control based on the button group being operated in the evaluation device of FIG. 1.

The content of the control will be described in detail with reference to FIG. 20.

FIGS. 20A and 20B are diagrams showing temporal changes in a signal to be input in the control unit 40 from the body motion sensor 31 along with a timing at which various buttons of the button group 10 are operated.

First, referring to FIG. 20A, the state of a signal acquisition stop flag is set to ON when a first operation is performed on the suspension button 10D at time T1 after the start of turning on the evaluation device 100, and input of the signal to the control unit 40 from the body motion sensor 31 (storage into the memory 42) is stopped.

When the suspension button 10D is then operated again at time T2, the state of the signal acquisition stop flag is set to OFF and input of the signal to the control unit 40 from the body motion sensor 31 (storage into the memory 42) is resumed.

In other words, in the evaluation device 100, if the suspension button 10D is not operated, the signal from the body motion sensor 31 are input constantly to the control unit 40 (without suspension after step S10 (FIG. 21)) and the input signal is stored in the memory 42.

When the go-to-bed button 10B is then operated at time T3, time T3 is stored in the memory 42 as the go-to-bed time.

When the good-night button 10C is then operated at time T4, the state of the measurement flag is set to ON, and the discrimination of sleep level is started.

When the good-night button 10C is then operated again at time T5, the state of the measurement flag is set to OFF, and the discrimination of sleep level ends.

When the suspension button 10D is then operated at time T6, the state of the signal acquisition stop flag is set to ON, and input of the signal from the body motion sensor 31 to the control unit 40 (storing into the memory 42) is stopped.

Furthermore, as a result of the suspension button 10D being operated, the signal detected by the body motion sensor 31 in the memory 42 is deleted from the point in time when the measurement flag was set to OFF immediately before this operation (time T5 in FIG. 20A) to the point in time when the suspension button 10D was operated (time T6 in FIG. 20A).

Note that in the present embodiment, although not only storing the signals detected by the body motion sensor 31 into the memory 42 but also inputting the detected signal to the control unit 40 are stopped when the state of the signal acquisition stop flag is set to ON, at least the storage of the detected signals into the memory 42 needs only be stopped.

Referring to FIG. 20B, when the good-night button 10C is operated at time T11 while the state of the signal acquisition stop flag is OFF and the state of the measurement flag is ON, the state of the measurement flag is set to OFF and detection of sleep level ends.

Thereafter, when the delete button 10A is operated at time T12, stored data of the signal detected by the body motion sensor 31 in the memory 42 is deleted from the point in time when the measurement flag was set to OFF immediately before this operation (time T11 in FIG. 20B) to the point in time when the delete button 10A was operated (time T12).

As described above, in the present embodiment, when the suspension button 10D or the delete button 10A is operated, stored data of the signal detected by the body motion sensor 31 in the memory 42 from the point in time when the measurement flag was set to OFF immediately before this operation to the point in time when each button was operated is deleted. Here, stored data of the detected signal corresponding to all periods before each button is operated may be deleted, not from the point in time when the measurement flag is set to OFF immediately before this operation.

Also, the discrimination of sleep level in the present embodiment may be performed at the same time as the acquisition of the signal detected by the body motion sensor 31, or may be performed at the point in time when an instruction indicating that various types of the display shown in FIGS. 10 to 12 and the like are performed is made. Furthermore, sleep level may be discriminated by the signal detected by the body motion sensor 31 in the memory 42 being transmitted to and processed by another computer.

Also, in the present embodiment, the CPU 41 receives information specifying the type of pre-sleep activity by a button in the button group 10 including the data processing button 10E being operated.

Note that the information specifying the type of pre-sleep activity may be input from another device, that is, may be input based on an input device connected to the evaluation device 100 being operated or the like.

In the evaluation device 100, the CPU 41 then discriminates the sleep level of a person being measured in response to the good-night button 10C being operated. In this example, the person being measured operates the good-night button 10C and thereby inputs information indicating that he/she intends to end the state before sleeping as information for specifying a timing at which discrimination of the state by discrimination means is started (timing specifying information). Also, as a result of discriminating the sleep level of the person being measured, the CPU 41 discriminates whether the person being measured is in the sleeping state or in the waking state. Note that for example, discriminating that the person being measured is in the above level 4 or level 5 corresponds to discriminating that the state of the person being measured is in the waking state. Also, discriminating that the person being measured is in any of the above levels 1 to 3 corresponds to discriminating that the state of the person being measured is in the sleeping state. Therefore, the person being measured can input an instruction to the input means at a point at which he/she enters the sleeping state on his/her own will after moving onto bedding so as to start the discrimination by the discrimination means. Therefore, with the evaluation device 100, a situation in which periods other than the period that the person being measured desires to evaluate (that is, discriminate sleep level) are evaluated can be avoided as much as possible, and thus the accuracy in evaluations of sleeping states performed by the sleep evaluation device can be improved.

Also, with the evaluation device 100, it is not necessary for various buttons of the button group 10 to be operated by the person being measured.

Also, with the evaluation device 100, a timing at which discrimination of sleep level is started or stopped is adjusted in accordance with the timing at which the good-night button 10C is operated. Note that at least one of a timing at which discrimination of sleep level is started and a timing at which that of sleep level is stopped (start time or stop time) may be stored in the memory 42 in advance. The CPU 41 then switches the state of the measurement flag between ON and OFF when each time that has been stored in the memory 42 has been reached so as to start or stop the discrimination of sleep level.

However, it is assumed that when "start time" to be stored in the memory 42 has been reached, the CPU 41 switches the state of the measurement flag to ON. In other words, if the state of the measurement flag is already ON when start time has been reached, the CPU 41 does not switch the state of the flag at this timing.

Also, it is assumed that when "stop time" to be stored in the memory 42 has been reached, the CPU 41 switches the state of the measurement flag to OFF. In other words, if the state of the measurement flag is already OFF when stop time has been reached, the CPU 41 does not switch the state of the flag at this timing.

The embodiments disclosed herein are to be considered in all respects as illustrative and not restrictive. The scope of the invention is not defined by the above description but by the claims, and all changes that come within the meaning and range of equivalency of the claims are intended to be embraced therein.

REFERENCE SIGNS LIST

- 10 button group
- 10A delete button
- 10B go-to-bed button
- 10C good night button
- 10D suspension button
- 10E data processing button
- 20 display unit
- 30 sensor
- 31 body motion sensor
- 40 control unit
- 41 CPU
- 42 memory
- 50 communication unit
- 100 evaluation device
- 200 display device
- 401 input unit
- 402 first discrimination unit
- 403 decision unit
- 404 generation unit
- 405 storage unit
- 406 readout unit
- 407 display control unit
- 408 communication control unit
- 409 second discrimination unit
- 4021 discrimination unit
- 4022 correction unit

The invention claimed is:

1. A sleep evaluation device comprising:
   a body motion detection device that detects body motion of a person being measured on a bed;
   a first operable device that generates a timing information at a first timing at which the person being measured is positioned on the bed;
   a second operable device that generates a timing information at a second timing at which the person being measured intends to go to sleep;
   a discrimination device that discriminates a sleeping state of the person being measured based on a detection result of the body motion detection device;
   said discrimination device further discriminating a predetermined sleep level of the sleeping state, said discrimination device setting a third timing in response to the discrimination of the predetermined sleep level; and
   an arithmetic operation device that calculates a first duration which is a duration from the first timing to the second timing, and a second duration which is a duration from the second timing to the third timing.

2. The sleep evaluation device according to claim 1, wherein the body motion detection device constantly detects the body motion of the person being measured on the bed.

3. The sleep evaluation device according to claim 1, further comprising:
   a body motion information storage device that stores information of the body motion detected by the body motion detection device; and
   an input device which receives information specifying a delete target period for which stored data of the body motion information is to be deleted from the body motion information storage device, wherein
   the sleeping state is discriminated based on the body motion information stored in the body motion information storage device, and
   stored data of information specifying the body motion corresponding to a delete target period is deleted from the body motion information storage device.

4. The sleep evaluation device according to claim 1, further comprising a period information storage device that stores information specifying a period during which the discrimination is performed by the discrimination device,
   wherein the discrimination device executes the discrimination in the period specified by the information stored in the period information storage device.

5. The sleep evaluation device according to claim 1, further comprising:
   a body motion information storage device that stores information on the body motion detected by the body motion detection device; and
   an input device which receives information that instructs the body motion detection device to suspend detection,
   the body motion detection device suspends, in response to information that instructs suspension of the detection being input to the input device, the detection of body motion, and
   the body motion information storage device deletes stored data of the body motion information stored before the information is input, in response to the information that instructs the suspension of the detection being input to the input device.

6. The sleep evaluation device according to claim 1, further comprising an input device which receives information that specifies a type of activity done by the person being measured in a period from the first timing to the second timing, and
   a display device which displays said type of activity along with the first duration and the second duration.

7. A sleep evaluation method that is executed on a sleep evaluation device including a body motion detection device that detects body motion of a person being measured on a bed, the sleep evaluation method comprising:
   detecting, by the body motion detection device, body motion of a person being measured on a bed;
   generating, by a first operable device, a timing information at a first timing at which the person being measured is positioned on the bed;
   generating, by a second operable device, a timing information at a second timing at which the person being measured intends to go to sleep;
   discriminating, by a discrimination device, a sleeping state of the person being measured based on the detection result of the body motion detection device;

discriminating, by the discrimination device, a predetermined sleep level of the sleeping state, and setting a third timing in response to the discrimination of the predetermined sleep level; and calculating, by an arithmetic operation device, a first duration which is a duration from the first timing to the second timing, and a second duration which is a duration from the second timing to the third timing.

8. The sleep evaluation device according to claim 2, further comprising:

a body motion information storage device that stores information on the body motion detected by the body motion detection device, wherein a sleeping state is discriminated based on the body motion information stored in the body motion information storage device.

9. The sleep evaluation device according to claim 1, further comprising:

a display device that displays the first duration and the second duration.

* * * * *